(12) United States Patent
Backhaus et al.

(10) Patent No.: US 8,090,593 B2
(45) Date of Patent: *Jan. 3, 2012

(54) MULTIPLE RESOURCE PLANNING SYSTEM

(75) Inventors: Brent Backhaus, Lakeville, MN (US); Lorna Lusic, Lakeville, MN (US); Dean Ebesu, San Francisco, CA (US)

(73) Assignee: Virtual Radiologic Corporation, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/084,379

(22) Filed: Apr. 11, 2011

(65) Prior Publication Data

US 2011/0191118 A1    Aug. 4, 2011

Related U.S. Application Data

(63) Continuation of application No. 12/783,073, filed on May 19, 2010, now Pat. No. 7,925,521, which is a continuation of application No. 11/288,645, filed on Nov. 28, 2005, now Pat. No. 7,729,928.

(60) Provisional application No. 60/656,215, filed on Feb. 25, 2005, provisional application No. 60/682,052, filed on May 17, 2005, provisional application No. 60/694,880, filed on Jun. 29, 2005, provisional application No. 60/699,119, filed on Jul. 14, 2005, provisional application No. 60/740,454, filed on Nov. 28, 2005, provisional application No. 60/740,589, filed on Nov. 28, 2005, provisional application No. 60/740,527, filed on Nov. 28, 2005.

(51) Int. Cl.
*G06Q 50/00* (2006.01)

(52) U.S. Cl. .......................................... 705/2

(58) Field of Classification Search .................. 705/2, 3, 705/4, 37; 707/10; 600/300.437; 364/413.01
See application file for complete search history.

(56) References Cited

U.S. PATENT DOCUMENTS 3,995,106 A    11/1976    Wern et al.
(Continued)

FOREIGN PATENT DOCUMENTS

WO    WO-01/99407 A1    12/2001
(Continued)

OTHER PUBLICATIONS

"24/7 Radiology Services", © 2003-2004. 24/7 Radiology, LLP. Retrieved from the Internet: <URL: http://www.247rad.comiservice.shtml>, (2004), 2 pgs.

(Continued)

*Primary Examiner* — Gerald J. O'Connor
*Assistant Examiner* — John Pauls
(74) *Attorney, Agent, or Firm* — Schwegman, Lundberg & Woessner, P.A.

(57) ABSTRACT

A system for managing remote doctor medical request workflow may include a workflow module that optimizes assignments of medical requests to remote doctors based on parameterized doctor and scheduling information and may further include a forecasting module that predicts the hospital credentials, state licenses or doctors needed to fulfill a projected volume of future medical requests. In one embodiment, radiologists are parameterized and then matched with requests for radiological readings based on information extracted from DICOM image headers and merged with associated information contained in a medical work order. In this embodiment, the radiologists are parameterized based on their locations, schedules, hospital credentials, state licensing, compensation metrics, and performance metrics and incoming requests for review of CT scans and the like are filtered based on the parameterized radiologist information to identify one or more radiologists who are to fulfill the medical request.

32 Claims, 7 Drawing Sheets

U.S. PATENT DOCUMENTS

| | | | |
|---|---|---|---|
| 4,003,023 | A | 1/1977 | Benson et al. |
| 4,058,835 | A | 11/1977 | Kennedy |
| 4,261,018 | A | 4/1981 | Knowlton |
| 4,302,775 | A | 11/1981 | Widergren et al. |
| 4,458,267 | A | 7/1984 | Dolazza |
| 4,463,386 | A | 7/1984 | Goddard et al. |
| 4,541,012 | A | 9/1985 | Tescher |
| 4,604,653 | A | 8/1986 | Shimizu |
| 4,614,978 | A | 9/1986 | Doster et al. |
| 4,622,585 | A | 11/1986 | Reitsma |
| 4,631,521 | A | 12/1986 | El-Sherbini |
| 4,652,933 | A | 3/1987 | Koshiishi |
| 4,748,511 | A | 5/1988 | Nichols et al. |
| 4,764,870 | A | 8/1988 | Haskin |
| 4,860,112 | A | 8/1989 | Nichols et al. |
| 4,910,609 | A | 3/1990 | Nicholas et al. |
| 5,216,596 | A | 6/1993 | Weinstein |
| 5,291,401 | A | 3/1994 | Robinson |
| 5,321,520 | A | 6/1994 | Inga et al. |
| 5,416,602 | A | 5/1995 | Inga et al. |
| 5,452,416 | A | 9/1995 | Hilton et al. |
| 5,469,535 | A | 11/1995 | Jarvis et al. |
| 5,513,101 | A | 4/1996 | Pinsky et al. |
| 5,631,953 | A | 5/1997 | Thomas et al. |
| 5,655,084 | A | 8/1997 | Pinsky et al. |
| 6,006,191 | A | 12/1999 | DiRienzo |
| 6,035,276 | A | 3/2000 | Newman et al. |
| 6,115,486 | A | 9/2000 | Cantoni |
| 6,137,527 | A | 10/2000 | Abdel-Malek et al. |
| 6,272,470 | B1 | 8/2001 | Teshima |
| 6,302,844 | B1 | 10/2001 | Walker et al. |
| 6,314,452 | B1 | 11/2001 | Dekel et al. |
| 6,381,029 | B1 | 4/2002 | Tipirneni |
| 6,424,996 | B1 | 7/2002 | Killcommons et al. |
| 6,448,956 | B1 | 9/2002 | Berman et al. |
| 6,473,524 | B1 | 10/2002 | Reda et al. |
| 6,481,887 | B1 | 11/2002 | Mirabella |
| 6,571,214 | B2 | 5/2003 | Newman et al. |
| 6,574,629 | B1 | 6/2003 | Cooke, Jr. et al. |
| 6,603,494 | B1 | 8/2003 | Banks et al. |
| 6,621,918 | B1 | 9/2003 | Hu et al. |
| 6,625,252 | B2 | 9/2003 | Mirabella |
| 6,678,703 | B2 | 1/2004 | Rothschild et al. |
| 6,798,533 | B2 | 9/2004 | Tipirneni |
| 6,820,057 | B1 | 11/2004 | Loch et al. |
| 6,876,759 | B2 | 4/2005 | Keller et al. |
| 6,915,266 | B1 | 7/2005 | Saeed et al. |
| 7,136,883 | B2 | 11/2006 | Flamma et al. |
| 7,500,185 | B2 | 3/2009 | Hu |
| 7,562,026 | B2 | 7/2009 | DelMonego et al. |
| 7,729,928 | B2 | 6/2010 | Backhaus et al. |
| 7,925,521 | B2 | 4/2011 | Backhaus et al. |
| 7,970,634 | B2 | 6/2011 | Backhaus et al. |
| 2001/0032215 | A1 | 10/2001 | Kyle et al. |
| 2001/0041991 | A1 | 11/2001 | Segal et al. |
| 2002/0016718 | A1 | 2/2002 | Rothschild et al. |
| 2002/0019751 | A1 | 2/2002 | Rothschild et al. |
| 2002/0065758 | A1 | 5/2002 | Henley |
| 2002/0087503 | A1 | 7/2002 | Judd et al. |
| 2002/0102012 | A1 | 8/2002 | Keller et al. |
| 2002/0102028 | A1 | 8/2002 | Keller et al. |
| 2002/0109859 | A1 | 8/2002 | Tipirneni |
| 2002/0161605 | A1 | 10/2002 | Newman et al. |
| 2002/0169637 | A1 | 11/2002 | Akers et al. |
| 2002/0198454 | A1 | 12/2002 | Seward et al. |
| 2003/0004409 | A1 | 1/2003 | Mueller et al. |
| 2003/0061090 | A1 | 3/2003 | Marano |
| 2003/0086595 | A1 | 5/2003 | Hu et al. |
| 2003/0149598 | A1 | 8/2003 | Santoso et al. |
| 2004/0064343 | A1 | 4/2004 | Korpman et al. |
| 2004/0117617 | A1 | 6/2004 | Geller et al. |
| 2004/0167402 | A1 | 8/2004 | Jones et al. |
| 2004/0186764 | A1 | 9/2004 | Mcneill |
| 2004/0254822 | A1 | 12/2004 | Mandelbaum |
| 2004/0257608 | A1 | 12/2004 | Tipirneni |
| 2005/0002483 | A1 | 1/2005 | Wilcox, Jr. |
| 2005/0075902 | A1 | 4/2005 | Wager et al. |
| 2005/0101856 | A1 | 5/2005 | Judd et al. |
| 2005/0114380 | A1 | 5/2005 | Eldar et al. |
| 2006/0053035 | A1 | 3/2006 | Eisenberg |
| 2006/0095423 | A1 | 5/2006 | Reicher et al. |
| 2006/0168338 | A1 | 7/2006 | Bruegl et al. |
| 2006/0195339 | A1 | 8/2006 | Backhaus et al. |
| 2007/0005798 | A1 | 1/2007 | Gropper et al. |
| 2010/0256986 | A1 | 10/2010 | Backhaus et al. |
| 2011/0004490 | A1 | 1/2011 | Backhaus et al. |
| 2011/0010192 | A1 | 1/2011 | Backhaus et al. |
| 2011/0015941 | A1 | 1/2011 | Backhaus |
| 2011/0066449 | A1 | 3/2011 | Backhaus et al. |

FOREIGN PATENT DOCUMENTS

| | | | |
|---|---|---|---|
| WO | WO-2010/087911 A1 | 8/2010 | |

OTHER PUBLICATIONS

"About HL7", Health Level Seven, [online]. [retrieved Jul. 15, 2005]. Retrieved from the Internet: <URL: www.hl7.org/about/about_nav_bar.cfm>, (2005), 15 pgs.

"About IHE", IHE Initiative: ACC/HIMSS/RSNA, [online]. [retrieved Jul. 15, 2005]. Retrieved from the Internet: <URL: http://www.ihe.net/About/index.cfm>, (2005), 2 pgs.

"About Us!", Emergency Radiology, [online]. [retrieved Nov. 2, 2006]. Retrieved from the Internet: <URL: http://www.emergencyradiology.net/aboutus.htm>, (2006), 1 pg.

"ACUO Technologies Products, ACUO Technology Product Webpage, Overview and Functionality data for (AcuoMed Image Manager & AcuoStore Digital Asses Manager)", ACUO Technologies, [online]. [retrieved Nov. 28, 2005]. Retrieved from the Internet: <URL: http://www.acuotech.com/acuoArchive.html>, (2005), 5 pgs.

"ACUO Technology DICOM Archive", ACUO Technologies, LLC. [retrieved Nov. 13, 2006], Retrieved from the Internet: <URL: http://www.acuotech.com/ acuoArchive.htrnl>, 3 pgs.

"American Radiology Offers Images Online to Referring Physicans", © American Radiology Services, Inc., [online]. [retrieved Feb. 23, 2005]. Retrieved from the Internet: <URL: http://www3.americanradiology.com/pls/web1/wwparticle.viewart?article_id_in=23>,(2003), 1 pg.

"American Radiology Services Nighthawk Services", American Radiology Services, Inc., [online]. © 2003. American Radiology Services, Inc. [retrieved Nov. 29, 2005]. Retrieved from the Internet: <URL: http://www3.americanradiology.com/pls/web1/wwreadserv.info>, (2003), 2 pgs.

"American Radiology Services Organization Information", American Radiology Services, Inc [retrieved on Feb. 25, 2005]., Retrieved from the Internet: <URL: http://www3.americanradiology.com/pls/webllwwaboutars.info >, (2003), 3 pgs.

"American Radiology Services, Inc.—Organization Information", [online]. [retrieved Feb. 25, 2005]. Retrieved from the Internet: <URL:http://www3.americanradiology.com/pls/web1/wwaboutars.info>, (2003), 3 pgs.

"APEX Radiology: A virtual Radiologist on Staff", © 2006 Apple Computer, Inc. [retrieved on Oct. 20, 2006], Retrieved from the Internet: <URL: http://www.apple.com/science/profiles/apexl>, (2006), 4 pgs.

"U.S. Appl. No. 11/288,645, Non Final Office Action mailed Nov. 12, 2009", 20 pgs.

"U.S. Appl. No. 11/288,645, Notice of Allowance mailed Mar. 24, 2010", 12 pgs.

"U.S. Appl. No. 11/288,645, Preliminary Amendment mailed Mar. 27, 2006", 4 pgs.

"U.S. Appl. No. 11/288,645, Response filed Feb. 12, 2010 to Non Final Office Action mailed Nov. 12, 2009", 13 pgs.

"U.S. Appl. No. 12/783,073, Notice of Allowance mailed Feb. 22, 2011", 9 pgs.

"U.S. Appl. No. 12/783,073, Preliminary Amendment mailed Jan. 10, 2011", 7 pgs.

"U.S. Appl. No. 12/882,479, Notice of Allowance mailed Mar. 23, 2011", 11 pgs.

"U.S. Appl. No. 12/882,479, Preliminary Amendment mailed Jan. 10, 2011", 10 pgs.

"Benefits", © 2004 Fujifilm UK, [Online]. [retrieved Nov. 28, 2005]. Retrieved from the Internet: <URL: www.fujifilm.co.uk/synapse/about/benefits>, (2004), 3 pgs.

"Cactus Advantage", Cactus Software, [online]. [retrieved Nov. 2, 2006]. Retrieved from Internet: <URL: http://www.visualcactus.com/Public2002/MCCACTUSAdvantageFull.htm>, (2006), 3 pgs.

"Cactus Software Products & Services", [online]. [retrieved Nov. 2, 2006]. Retrieved from the Internet: <URL: http://www.visualcactus.com/Public2002/HomeFramedPage.htm>, 1 pg.

"California Radiographics Homepage", California Radiographics Inc., [online]. [retrieved Feb. 25, 2005]. Retrieved from the Internet: <URL: http://www.nightshiftradioiogy.com/teleradiology_equipment.htm>, (2005), 4 pgs.

"Cascadable Architecture", © 2004 Fujifilm UK, [online]. [retrieved Nov. 11, 2006]. Retrieved from the Internet: <URL: www.fujifiim.co.uk/synapse/product/cascadable>, (2004), 2 pgs.

"Case Studies EchoApps", © 2006 Healthline Systems Inc., [online]. [retrieved Nov. 2, 2006]. Retrieved from the Internet: <URL: http://www.healthlinesystems.com/casestudies/echoapps_mc.asp>, (2006), 5 pgs.

"Chatham Radiology Group Deploys Neurostar's Virtual Radiology Network Solution to Improve Service and Productivity", Neurostar Solutions, [online]. [retrieved Apr. 26, 2005]. Retrieved from the Internet: <URL: www.neurostarsolutions.com/index/jsp?page=PressRelease&newsID=2>, (2003), 3 pgs.

"Comply Product Overview", Strategic Management Group LLC, [online]. [retrieved Nov. 2, 2006]. Retrieved from the Internet: <URL: http://www.complysoftware.com/>, 2 pgs.

"Credentialing Software from Intellisoft", Intellisoft Group, Inc, [online]. [retrieved: Nov. 2, 2006]. Retrieved from the Internet: <URL: http://www.intellisoftgroup.com/>, 3 pgs.

"Database Management System", Fujifilm UK, [online]. [retrieved Nov. 28, 2005]. Retrieved from the Internet: <URL: www.fujifilm.co.uk/synapse/technical/database>, (2004), 1 pg.

"Desktop User Interface", © 2004 Fujifilm UK, [online]. [retrieved Nov. 28, 2005]. Retrieved from the Internet: <URL: www.fujifilm.co.uk/synapse/product/desktop>, (2004), 2 pgs.

"Developing the Complete Teleradiology Infrastructure", The Hawk—The NightHawk Radiology Services Newsletter, (2005), 2 pgs.

"Diagna Radiology", [online]. [retrieved Feb. 25, 2005]. Retrieved from the Internet: <URL: http://www.diagna.com/>, (Feb. 25, 2005), 12 pgs.

"DICOM Conformance Statement for Cedara I-SoftView", Cedara Software Corp, Document No. 2004-02987, (2005), 1-38.

"EchoApps", Healthline Systems Inc., [online]. [retrieved Sep. 6, 2005]. Retrieved from the Internet: <URL: http://www.healthlinesystems.com/echoapps_mc.asp>, (2005), 3 pgs.

"EchoApps—Simplify the Provider Application Process", © 2004 HealthLine Systems Inc [retrieved on Nov. 28, 2005]. Retrieved from the Internet: <URL: http://echomc.comlechoappsprocess2.asp>, (2004), 2 pgs.

"EchoApps Quick Tour, 12 Screen Captures", HealthLine Systems Inc., [online]. [retrieved Nov. 28, 2005]. Retrieved from the Internet: <URL: http://healthlinesystems.com/demos/echoapps_demo.htm>, (2005), 13 pgs.

"EHR Clinical Overview", U.S. Department of Health and Human Services—Indian Health Service, [online]. [retrieved Jul. 15, 2005]. Retrieved from the Internet: <URL: http://www.ihs.gov/CIO/EHR/index.cfm?module=clincaloverview>, (2005), 2 pgs.

"eMed—Test Drive Register", © 2003 eMed(r) Technologies, [online]. [retrireved Jul. 15, 2005]. Retrieved from the Internet: <URL: www.emed.com/products_services/matrix.php>, (2003), 4 pgs.

"Emergency Radiology Home Page", [online]. [retrieved Nov. 12, 2006]. Retrieved from the Internet: <URL: http://www.emergencyradiology.net/missionstatement.htm>, 1 pg.

"Enterprise Image Management", © 1997-2004. GE Medical Systems. [online]. [retrieved Jul. 15, 2005]. Retrieved from the Internet: <URL: www.gehealthcare.com/img_info_systems/centricity_ris/products/enterprise_img.html>, 2 pgs.

"Epic Teleradiology Services", © 2006 Epic Teleradiology, [online]. [retrieved Nov. 2, 2006]. Retrieved from the Internet: <URL: http://www.epictele.com/services.php>, (2006), 1 pg.

"European Application Serial No. 94908280.4, Entscheidung, vol. 9, Board of Appeal of the European Patent Offic e", (Feb. 2005), 19 pgs.

"External Information System", © 2004 Fujifilm UK, [online]. [retrieved Nov. 28, 2005]. Retrieved from the Internet: <URL: www.fujifilm.co.uk/synapse/technical/external>, (2004), 2 pgs.

"Fuji Receives Patent for Synapse's Subscription Technology", Fujifilm Medical Systems USA, [online]. [retrieved Jul. 18, 2005]. Retrieved from the Internet: <URL: http://www.fujimed.com/company-info/press-room/doc/press_subscription_technology.asp?location=3&area=25&id=0&subid=0, (2005), 2 pgs.

"Healthline Medical Imaging Modality Worklist DICOM Conformance Statement", Healthline Medical Imaging, (2005), 1-16.

"Healthline Medical Imaging Specification DICOM Conformance Statement", Healthline Medical Imaging, (2005), 27 pgs.

"HL7 Communications Module Definition Statement", © 2000-2005 Healthline Information Systems, Inc., (2005), 1-41.

"Home work may solve doc shortage", May, [retrieved Nov. 22, 2007], Retrieved from the Internet: <URL: www.usrp.net/articles/Home work.htrnl>, 2 pgs.

"IDX® Imagecast tm Image Management—Radiology", [online]. © 1999-2005 IDX Systems Corporation. [retrieved Jul. 15, 2005]. Retrieved from the Internet: <URL: www.idx.com/imagecast/ic_im_rad.asp>, (2005), 3 pgs.

"IHE Cardiology Technical Framework Supplement 2005—Displayable Reports (DRPT)", © 2005 ACC/HIMSS/RSNA, (2005), 1-41.

"IHE Organization", IHE initiative: ACC/HIMSS/RSNA, [online]. [retrieved Nov. 30, 2005]. Retrieved from the Internet: <URL: http://www.ihe.net/About/Organization/org.cfm>, (2005), 3 pgs.

"Image Display Workstations", © 2004 Fujifilm UK, [Online]. [retrieved Nov. 28, 2005]. Retrieved from the Internet: <URL: www.fujifilm.co.uk/synapse/technical/display>, (2004), 2 pgs.

"Images Acquisitions System", © 2004 Fujifilm UK, [Online]. [retrieved Nov. 28, 2005]. Retrieved from the Internet: <URL: www.fujifilm.co.uk/synapse/technical/image>, (2004), 2 pgs.

"Images to any Desktop with Synapse", Synapse Intelligent Connectivity, Fujifilm Medical Systems USA, (2003), 2 pgs.

"Imaging on Call Is a JCAHO Accredited Facility", © 2005 Imaging on Call, LLC, [online]. [retrieved Nov. 3, 2006]. Retrieved from the Internet: <URL: http://www.imagingoncall.net/company/jcaho.php>, (2005), 1 pg.

"Integrated Web Technology", © 2004 Fujifilm UK, [online]. [retrieved Nov. 28, 2005]. Retrieved from the Internet: <URL: www.fujifilm.co.uk/synapse/product/webtechnology>, (2004), 2 pgs.

"International Application Serial No. PCT/US05/43212, International Search Report mailed Sep. 26, 2007", 7 pages.

"International Application Serial No. PCT/US05/43212, Written Opinion mailed Sep. 26, 2007", 4 pgs.

"Medical Licensure Services", Medlicense.com. [retrieved on Sep. 7, 2005]. Retrieved from the Internet: <URL: http://www.medlicense.comlservoces.html>, (2005), 3 pgs.

"MedModel—The Industry Standard for Healthcare Simulations", [online]. © 2002-2004. Healthcare Planning Associates. [retrieved Sep. 7, 2005]. Retrieved from the Internet: <URL: http://www.promodel.com/products/medmodel>, 2 pgs.

"MedModel Simulation Plan your hospital and clinics using simulation software", © 2002-2004. Healthcare Planning Associates, [online]. [retrieved Nov. 29, 2005]. Retrieved from the Internet: <URL: http://www.hpa.co.nz/index.asp'?fpar=13732555342>, (2005), 2 pgs.

"Misys PACS Integration Module (PIM)", © 2004 Misys Hospital Sytems, Inc., [online]. Retrieved from the internet: <URL: http://www.misyshealthcare.com/NR/rdonlyres/11B3E4E4-B08B-4A78-970E-D37B8B69CCBF/0/misysPIMrev4.pdf#search=%22Misys%20PACS%20Integration%20Module%20(PIM)%22>, (2004), 2 pgs.

"Mobile Imaging", Empire Teleradiology Associates, LLC, [online]. [retrieved Oct. 13, 2006]. Retrieved from the Internet: <URL: http://www.empiretelerad.com/emp_mobile.htm>, (2002), 1 pg.

"Multi-Site PACS with Synapse", Synapse Intelligent Connectivity, Fujifilm Medical Systems USA, (2003), 2 pgs.

"National Practitioner Data Bank Healthcare Integrity and Protection Data Bank", NPDB-HIPDB, [Online]. Retrieved from the Internet: <URL: http://www.npdb-hipdb.com/npdb.html> Accessed on Jul. 18, 2005, 3 pgs.

"Network", © 2004. Fujifilm UK. [retrieved on Nov. 28, 2005]., Retrieved from the Internet: <URL: www.fujifilm.co.uk/synapse/technicaVnetwork>, (2004), 2 pgs.

"Night and Weekend Call Service", RadLinx Group, [online]. Retrieved from the Internet: <URL: http://www.radlinxgroup.com/nighthawk.html>, 3 pgs.

"Night Shift Radiology", Schematic of NightShift Radiology Network. NightShift Radiology, 2005 [retrieved on Feb. 25, 2005], [Online]. Retrieved from the Internet: <URL: http://www.nightshiftradiology.comlnetwork.htm>, 2 pgs.

"Nighthawk Pros Premier Night-Time Coverage—NightHawk Pros Company Profile, Teleradiology Overview of Services, Teleradiology Solutions for Radiology Experts, Teleradiology Technology Solutions", Nighthawk Pros, [online]. [retrieved Feb. 25, 2005]. Retrieved from the Internet: <URL: http://www.nighthawkpros.com/>, 4 pgs.

"Nighthawk Radiology Services contact information—contact information, company information, services, network technology", Nighthawk Radiology Services, [online]. [retrieved Feb. 25, 2005]. Retrieved from the Internet: <URL: http://www.nighthawkrad.net/>, 5 pgs.

"NightRays credentialing", NightRays, [retrieved on Oct. 13, 2006], Retrieved from the Internet: <URL: http://www.nightrays.comlcredreq.pdf>, 1 pg.

"NightShift Radiology—Overview", NightShift Radiology, [online]. [retrieved Feb. 25, 2005]. Retrieved from the Internet: <URL: http://www.nightshiftradiology.com/>, (2005), 3 pgs.

"Nightshift Radiology Our Network: Built for Reliability", Nightshift Radiology, [online]. [retrieved Nov. 28, 2005]. Retrieved from the Internet: <URL: http://www.nightshiftradiology.com/network.htm>, (2005), 2 pgs.

"NightShift Radiology Preliminary Report, Sample Report", Nightshift Radiology, [online]. [retrieved Feb. 25, 2005]. Retrieved from the Internet: <URL: http://www.nightshiftradiology.com/sample_report.htm>, (2005), 6 pgs.

"Non-Emergency Solve the Demand for Radiologists", © 2006 Diagna Radiology, [online]. [retrieved Nov. 3, 2006]. Retrieved from the Internet: <URL: www.diagna.com/nonemerg.htm>, (2006), 2 pgs.

"On Demand Access to data", © 2004 Fujifilm UK, [online]. [retrieved Nov. 28, 2005]. Retrieved from the Internet: <URL: www.fujifilm.co.uk/synapse/product/ondemand>, (2004), 2 pgs.

"OneApp Credentialing Software", SyMed, 2005 [retrieved on Sep. 7, 2005]. Retrieved from the Internet: <URL: http://www.symed.comlproducts/oneapp>, (2005) 2 pgs.

"OneApp Product Tour", SyMed, 2005 [online]. [retrieved on Nov. 22, 2004], Retrieved from the Internet: <URL: http://www.symed.comlproducts/oneapptour-l.asp>, 6 pgs.

"Partners you can trust", International Teleradiology Corporation, [retrieved Nov. 3, 2006], Retrieved from the Internet: <URL: http://www.teleradiologyonline.comlindex.htm>, (2006), 1 pg.

"Product Data AON Tool Set Software Release Version 3.0", Fujifilm Medical Systems, (2003), 2 pgs.

"Product Data Server Software Release Version 3.0", Synapse Intelligent Connectivity, Fujifilm Medical Systems USA, Inc., (2003), 2 pgs.

"Project Title: Developing a Prototype for a Nationwide Health Information Network Architecture,", Request for Proposal (RFP) ONCHIT-3, Section C Descriptions/Specifications/Work Statement, (published prior to Nov. 10, 2010), 9 pgs.

"PROS CAN Reading Services World Leaders in Medical Imaging Interpretation", Proscan Reading Services, [retrieved on Oct. 20, 2006], Retrieved from the Internet: <URL: http://www.proscan.comlfw/mainlfw_link.asp?URL=/ _filelib/FileCabinet/PDF IProScanReadingService. pdfOlo3FFileName%3DProScanReadingService.pdf &Titie=Reading%20Services%20Brochure>, (2006), 9 pgs.

"Radiology is Going Places Let Us Take You There First", CMP Healthcare Media Group LLC, 2005, [retrieved Nov. 30, 2005], Retrieved from the Internet: <URL: www.diagnosticimaging.com >, 4 pgs.

"Radiology PACS RadWorks 5.0 Standard", Wipro GE Healthcare, [online]. [retrieved Jul. 15, 2007]. Retrieved from the Internet: <URL: www.gehealthcare.com/inen/it_solutions/r ad_ pacs/ products/rad/msiisrwst2.html.html>, 3 pgs.

"Radiology PACS RadWorks 5.1 Standard", Wipro GE Healthcare, [retrieved on Jul. 15, 2005], Retrieved from the Internet: <URL: www.gehealthcare.comlineniit solutions/radpacs/products/radlradworks.html>, 2 pgs.

"Rapid Reliable Radiology Technology", StatRad. [retrieved on Oct. 27, 2006]. Retrieved from the Internet: <URL: http://statrad.comltechnology.html>, 2 pgs.

"Rapid Response Radiology", © 2006 Consulting Radiologists, Ltd., [retrieved on Nov. 3, 2006], Retrieved from the Internet: <URL: http://www.consultingradiologists.com/rapidresponsetechnology.htrn >, 1 pg.

"RIS Radiology Information System Online Data Entry for Nighttime Teleradiology Studies", Startup Guide v1.7, Virtual Radiologic Consultants, (May 16, 2005), 9 pgs.

"RSI Difference", (published prior to Nov. 10, 2010), 3 pgs.

"Santa Barbara County Care Data Exchange", Santa Barbara County Care Data Exchange, Located: <URL: http://www.chcf.org/documents/ihealthJSantaBarbaraFSWeb.pdf.>, 4 pgs.

"SkyRIS TeleRIS—Complete workftow, reporting and distribution solution for multi-contract radiology and teleradiology", ThinAir Data, Los Angeles, CA, (2004), 2 pgs.

"SkyRISE Enterprise—Enterprise speech recognition interfaced to existing HIS/RIS", ThinAir Data, Santa Monica, CA, (2004), 2 pgs.

"Software Solutions for Today's Healthcare Professionals", Morrisey Associates, 2006 [retrieved on Nov. 3, 2006], Retrieved from the Internet: <URL: http://www.morriseyonline.com>, 1 pgs.

"Special Report: What's all the noise about tele-radiology?", RadLinx Group, [retrieved on Nov. 29, 2005], Retrieved from the Internet: <URL: http://www.radlinxgroup.com/ articie noise teleradiology.html>, 3 pgs.

"StatRAD—Rapid, Reliable Radiology", Welcome, About Us, Services, Jobs, Contact [online]. Stat Radiology, [retrieved on Feb. 25, 2005], Retrieved from the Internet: <URL: http://statrad.comlindex.html>, 9 pgs.

"Storage System", Fujifilm UK, 2004, [retrieved on Nov. 28, 2005], Retrieved from the Internet: <URL: www.fujifilmco.ukJsynapse/technicaVstorage>, 2 pgs.

"Sy Med Simplifying Managed Care", Sy.Med Development, Inc., 2006 [retrieved on Nov. 3, 2006], Retrieved from the Internet: <URL: http://www.symed.coml>, 1 pg.

"Synapse User's Manual Quick Reference Guide", Software Version 3.0.0,2002, Fujifilm Medical Systems USA, Inc., (2002), 198 pgs.

"Synapse Version 3.0.0 Systems Administration Manual", Fujifilm, (2003), 1-55 pgs.

"Synapse™ Version 3.0.0 Workstation Administration Manual", Fujifilm, (2004), 1-62.

"TDS Network Welcome", Teleradiology Diagnostic Service, 2004, [retrieved on Oct. 27, 2006], Retrieved from the Internet: <URL: http://www.tdsnetwork.neti>, (2004), 2 pgs.

"Technical Features", Fujifilm UK, 2004, [retrieved on Nov. 28, 2005]., Retrieved from the Internet: <URL: www.fujifilm.co.uk/synapse/technical>, (2004), 2 pgs.

"Technically, It's Important", TeamHealth Radiology, 2006, [retrieved on Oct. 27, 2006]. Retrieved from the Internet: <URL: http://www.thteleradiology.comltechnology.htrn>, 3 pgs.

"Teleradiology Solutions about us, services, contact us", Teleradiology Solutions, 2002 [retrieved on Feb. 25, 2005], Retrieved from the Internet: <URL: http://www.telradsol.coml >, (2002), 4 pgs.

"Teleradiology: At Work Night and Day", Harris, 2006, [retrieved on Nov. 3, 2006]., Retrieved from the Internet: <URL: www.healthimaging.comlcontent/view/479/681>, (2006), 5 pgs.

"TeleShare", Dejarnette Research Systems, 2005, [retrieved on Sep. 7, 2005], Retrieved from the Internet: <URL: http://www.dejarnette.comll024/requestedpage.asp?Content=Products/>, (2004), 2 pgs.

"Templeton Radiology", Templeton Readings LLC, 2004 [retrieved on Feb. 25, 2005]., Retrieved from the Internet: <URL: http://www.templetomadiology.coml >, (2004), 9 pgs.

"Templeton Radiology Night Solutions", Templeton Radiology, 2004, [retrieved on Sep. 7, 2005], Retrieved from the Internet: <URL: http://www.templetomadiology.comlnight_so1.htrn>, 2 pgs.

"Templeton Radiology Physician Credentialing", Templeton Radiology, 2004, [retrieved on Sep. 7, 2005], Retrieved from the Internet: <URL: http://www.templetomadiology.comlpc.htrn>, 2 pgs.

Templeton Radiology Radiology Services, Templeton Radiology, [retrieved on Nov. 29, 2005], Retrieved from the Internet: <URL: http://www.idshealthcare.com/hospital_management/global/templeton_radiology/web_enabled dictation!..>, 3 pgs.

Templeton Radiology RISIPACS website product information, Templeton Radiology, [retrieved on Nov. 29, 2005], Retrieved from the Internet: <URL: http://www.templetomadiology.comlpacs.htrn>, 2 pgs.

Templeton Radiology RISIPACSIWEB/ARCHIVE managed solution, Templeton Radiology, 2004, [retrieved on Nov. 29, 2005], Retrieved from the Internet: <URL: http://www.templetomadiology.comlpacs.htrn>,, 6 pgs.

Templeton Radiology Teleradiology Night Solutions, Templeton Radiology, [retrieved Nov. 29, 2005], Retrieved from the Internet: <URL: http://www.idshealthcare.comlhospitat management/global/templeton radiology/templeton_mobile readings/.htrn>, 3 pgs.

The Project, GlobalRad® Non-Profit Foundation [retrieved Nov. 3, 2006] Retrieved from the Internet: <URL: http://www.globalrad.org/project.htrn>, 1 pg.

The RadLinx Group Ltd.—FAQ's, [online]. [retrieved Nov. 29, 2005]. Retrieved from the Internet: <URL: http://www.radlinxgroup.com/faq.html>, 2 pgs.

The Work Flow Process, Imaging on Call, LLC, [retrieved Nov. 3, 2006]., Retrieved from the Internet: <URL: http://www.imagingoncall.net/technology/sat.php>, (2005.), 1 pg.

"ThinAir Data—Healthcare at the Speed of Thought", [online]. [archived Nov. 11, 2004]. Retrieved from the Internet: <URL: http://web.archive.org/web/20041112045011/http://www.thinairdata.com>, (2004), 2 pgs.

"To the ends of the Earth", Page, Diagnostic Imaging, [retrieved on Feb. 25, 2005]., Retrieved from the Internet: <URL: www.diagnosticimaging.com/specialedition2003I? page=teleradiology.htrnl >, (2003), 7 pgs.

"U.S. Based Client Services", RadLinx Group, [retrieved on Nov. 29, 2005], Retrieved from the Internet: <URL: http://www.radlinxgroup.comlc1ient.htrnl>, 2 pgs.

"US Radiology On-Call", Locations, Services, Technology, Radiologists, FAQ, Contact Us, [online]. [retrieved Feb. 25, 2005]. Retrieved from the Internet: <URL: http://www.usroc.coml>, 7 pgs.

"US Radiology On-Call—Locations, Services, Technology, Radiologists, FAQ, Contact Us", [online]. [retrieved Feb. 25, 2005]. Retrieved from the Internet: <URL: http://www.usroc.com/>, 7 pgs.

"US Radiology On-Call FAQ", US Radiology On-Call, [retrieved on Nov. 3, 2006], Retrieved from the Internet: <URL: http://www.usroc.comlfaq.htrnl>, 2 pgs.

"US Radiology On-Call Radiologists", US Radiology On-Call, [retrieved on Nov. 3, 2006], Retrieved from the Internet: <URL: http://www.usroc.comlradiologists.htrnl>, 1 pg.

"Veritas Product", Veritas Product data (V-FORM) [online]. © 2003 Veritas Medical Services, Inc., [retrieved on Sep. 7, 2005], Retrieved from the Internet: <URL: http://www.veritasmed.comlproducts/>,, 3 pgs.

"Virtual Radiologic Physician Services Operating Manual", Virtual Radiologic Consultants, Inc., (2005), 75 pgs.

"Vistar Technologies—Automated Credentialing Software CVOs and Medical Societies", Vistar Technologies, 2005 [retrieved Nov. 3, 2006], Retrieved from the Internet: <URL: http://vistartech.comlcvomed.htrn >, (2005.), 1 pg.

"Visual Cactus", Cactus Software, [retrieved Oct. 25, 2006], Retrieved from the Internet: <URL: http://www.visualcactus.comlPublic2002/images/HospitalFlyer-2005.pdf.>,, 1 pg.

"VRN—A step Beyond Teleradiology", NeuroStar Solutions, 2005, [retrieved Nov. 30, 2005], Retrieved from the Internet: <URL: http://www.neurostarsolutions.com/cms/theVRN/vrnApplicationServices/pacs.html?, (2005), 2 pgs.

"Welcome to MedTel International", MedTel International, [retrieved on Nov. 3, 2006], Retrieved from the Internet: <URL: http://www.medtel.coml >,, 1 pg.

"Why the NPDB Was Created", National Practioner Data Bank (NPDB) [retrieved on Nov. 30, 2005], Retrieved from the Internet: <URL: http://www.npdb-hipdb.comlnpdb.htrnl>, 2 pgs.

"WIN/Staff PRO-FILE", WIN/Staff, [retrieved Nov. 3, 2006], Retrieved from the Internet: <URL: http://www.winstaff.comlmarketing/prac J>ro file.htrn >, (2002), 1 pgs.

"World Wide Rad FAQ", World Wide Rad, [retrieved on Nov. 3, 2006], Retrieved from the Internet: <URL: http://www.worldwiderad.comlWWRWebsite files/frame.htrn >, 1 pg.

Batchelor, J. S., "Remote-controlled MRI tackles tech shortage", AuntMinnie.com, 2006, [retrieved on Jan. 26, 2006], Retrieved from the Internet: <URL: http://www.auntrninnie.comlindex.asp?sec=ser&sub=def&pag=dis&ItemID=69371>, (2006), 2 pgs.

Brice, J., "Continued IT evolution boosts teleradiology", Nighthawk in the news, NightHawl Services, Diagnostic Imaging, (Feb. 2004), 5 pgs.

Harrell, C. R., et al., "Healthcare Simulation Modeling and Optimization using MedModel", *Proceedings of the 2000 Winter Simulation Conference*, 2000, Joines et al., eds., (2000), 203-207.

Skyris, "Full feature RIS with integrated speech recognition and transcription", ThinAir Data, Santa Monica, CA, (2004), 2 pgs.

Thinair Data, Skyris Teleradiology, "TeleRIS is the complete teleradiology, multi-contract, multi-facility workftow, reporting and distribution solution", Los Angeles, CA, http://web.archive.org/web/200502040552131/www.thinairdata.com/SkyRISTele.htm, (2005), 3 pg.

"ExParte Reexamination Request mailed Dec. 17, 2010 in re: Backhaus et al., Patent No. 7,729,928", (Dec. 17, 2010).

Collins, J E, et al., "IEEE Reference: Automated Assignment and Scheduling of Service Personnel", 3M Company, p. 35, (Apr. 1994).

Khan, Rashid N, "Business Process Management: A Practical Guide", (Sep. 2004), 103-124.

Khan, Rashid N, "Business Process Management: A Practical Guide", (Sep. 2004), p. 179.

Khan, Rashid N, "Business Process Management: A Practical Guide", (Sep. 2004), 207-222.

Khan, Rashid N, "Business Process Management: A Practical Guide: Smart Ways of Routing Work (Excerpt)", (Sep. 2004), 1-4.

MULTIPLE RESOURCE PLANNING SYSTEM

CROSS REFERENCE TO RELATED CASES

This application is a continuation of U.S. patent application Ser. No. 12/783,073, filed on May 19, 2010 which is a continuation of prior U.S. patent application Ser. No. 11/288,645 filed Nov. 28, 2005 and entitled "Multiple Resource Planning System", which claims the benefit of U.S. Provisional patent application Nos. 60/656,215, filed Feb. 25, 2005 by Backhaus and entitled "Automated Credentialing and Licensing System"; 60/682,052, filed May 17,2005, by Backhaus et al, and entitled "Integrated Caching Environment with Order Form Pre-population"; 60/694,880, filed Jun. 29, 2005, by Backhaus et al., and entitled "Medical Data Management Method and System"; 60/699,119, filed Jul. 14, 2005, by Backhaus et al., and entitled "Medical Data Transfer System and Method"; 60/740,454, filed Nov. 28, 2005 by Backhaus et al., and entitled "Medical Data Transfer System and Method"; 60/740,589, filed Nov. 28, 2005 by Casey and entitled "Remote Scanning System and Method"; and 60/740,527, filed Nov. 28, 2005 by Casey and entitled "Patient Information Translation Method and System"; the entirety of which are incorporated herein by reference.

BACKGROUND

Medical images, such as X-rays, CAT (computerized axial tomography) scans, and MRI's (Magnetic Resonance Imaging), may be digitized to facilitate remote reading by doctors. A hospital may use systems that capture and digitize the images and transmit them to a remote image server, such as a Picture Archiving and Communications System (PACS). The transmission may occur over a network, such as an intranet or the Internet.

Additionally, the hospital may also transmit orders corresponding to the images to an order server, such as a Radiologist Information System (RIS). The orders may be requests for a doctor to interpret, or read, the images and return a diagnostic report. Orders may also contain information, such as a patient identifier, the procedure type associated with the image, patient demographic information, and a hospital identifier.

Some systems route the images and orders to doctors in a fixed manner. For example, all of the images and orders may be transmitted from the scanning area of a hospital to a set of doctors that work in the radiology department of the same hospital. The doctors may be at the hospital or at remote systems. Other systems route the images and orders to doctors based on data included in the image headers, such as information about the body area that is scanned. For example, if the image header includes information that specifies that the image is a head scan, the image and the associated order may be transmitted from the scanning area of the hospital to doctors that work in the neurology department of the hospital instead of to doctors that work in the urology department.

After receipt of the images and orders, the radiologist may analyze the image and return the diagnostic report using the remote system. The diagnostic report may be transmitted through the network to the order server, which may send the report to the hospital or other medical facility that originally transmitted the order and images corresponding to the report.

Synapse from FUJIFILM Medical Systems, Stamford, Conn. allows doctors to subscribe to a folder on a PACS. When new content arrives in that folder, a doctor receives notification that the content has arrived. The new content may be cached or stored on the doctor's remote system for viewing.

SUMMARY

A system for managing remote doctor medical request workflow may include a workflow module that optimizes assignments of medical requests to remote doctors based on parameterized doctor and scheduling information and may further include a forecasting module that predicts the hospital credentials, state licenses or doctors needed to fulfill a projected volume of future medical requests. In one embodiment, radiologists are parameterized and then matched with requests for radiological readings based on information extracted from DICOM image headers and merged with associated information contained in a medical work order. In this embodiment, the radiologists are parameterized based on their locations, schedules, hospital credentials, state licensing, compensation metrics, and performance metrics and incoming requests for review of CT scans and the like are filtered based on the parameterized radiologist information to identify one or more radiologists who are to fulfill the medical request. In other embodiments, the system forecasts a shortfall or excess in the number of hospital credentials, state licenses, or radiologists needed to fulfill a projected future volume of medical requests based on workflow assignment parameters that include radiologist work schedules, expected licensing approvals, expected credentialing approvals, medical facility preferences for certain doctors, radiologist contract terms, radiologist compensation metrics, historical radiologist performance metrics, and additional medical facilities to be serviced during the future time period.

DESCRIPTION OF DRAWINGS

Like reference symbols in the various drawings indicate like elements.

DETAILED DESCRIPTION OF ILLUSTRATIVE EMBODIMENTS

Figure 1:
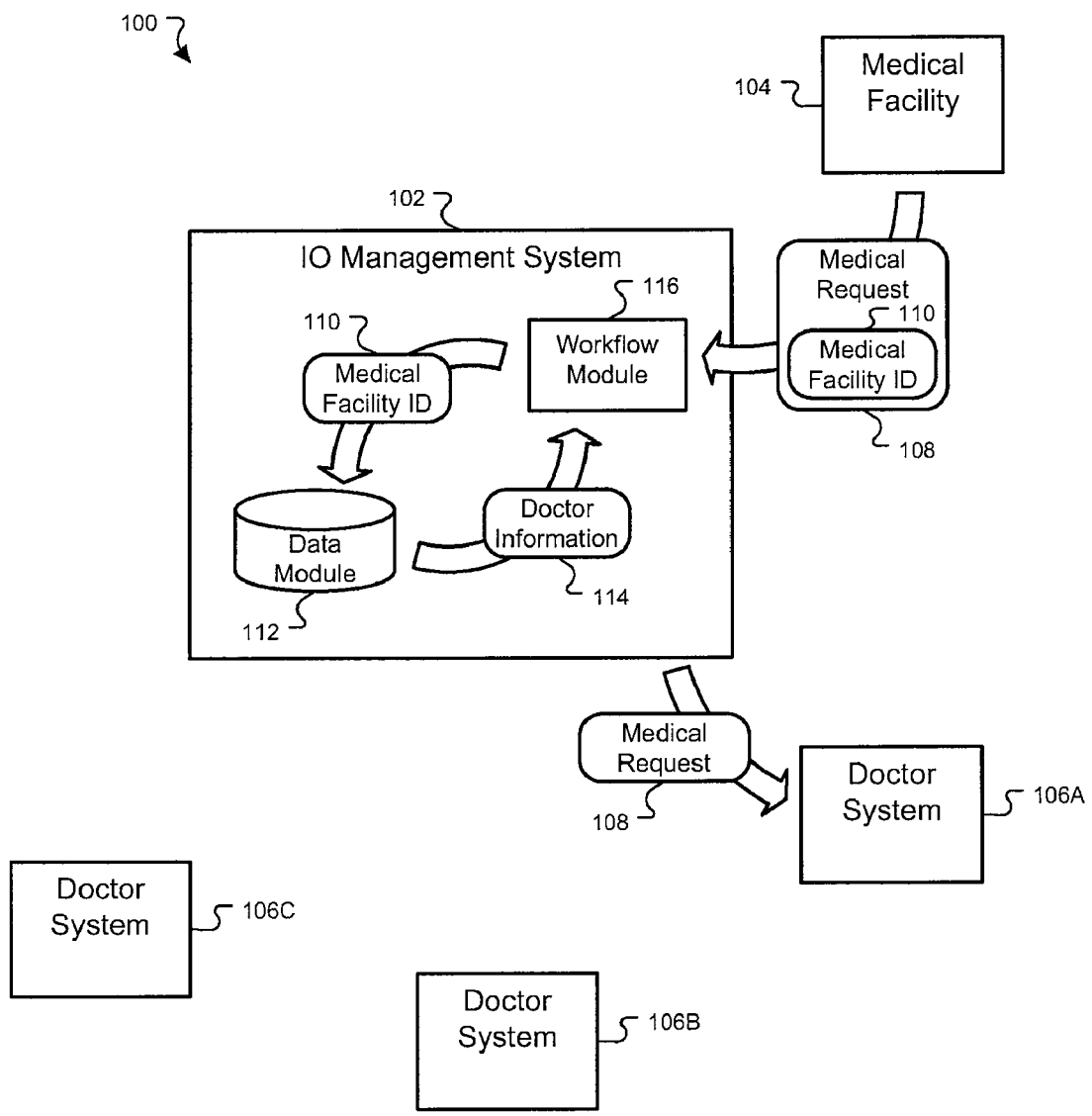
FIG. 1 is an exemplary block diagram of a system for assigning medical requests to doctor systems.

FIG. 1 shows an exemplary system 100 for assigning medical requests to doctor systems. Medical facilities transmit the medical requests to an Image Order (IO) management system, which implements a workflow module that assigns the medical requests to selected doctors. The assignment may be based on several variables, such as whether the doctor is credentialed at the hospital, the doctor's schedule, the preference of the hospital for certain doctors, doctors' licensing status, compensation metrics, online status, geography, performance, and the complexity of previous medical requests that have been assigned to a doctor. After assignment, the IO management system transmits the requests to the assigned doctor.

To implement the medical request assignment, the system 100 includes an image order (IO) management system 102, a medical facility 104, and doctor systems 106A-C. The IO management system 102 performs operations to route medical requests from medical facilities, such as the medical facility 104, to one or more of the doctor systems 106A-C. The IO management system 102 receives a medical request 108, which includes a medical facility identifier (ID) 110, from the medical facility 104, The medical facility ID 110 is associated with the medical facility 104 from which the medical request 108 originated.

Figure 3:
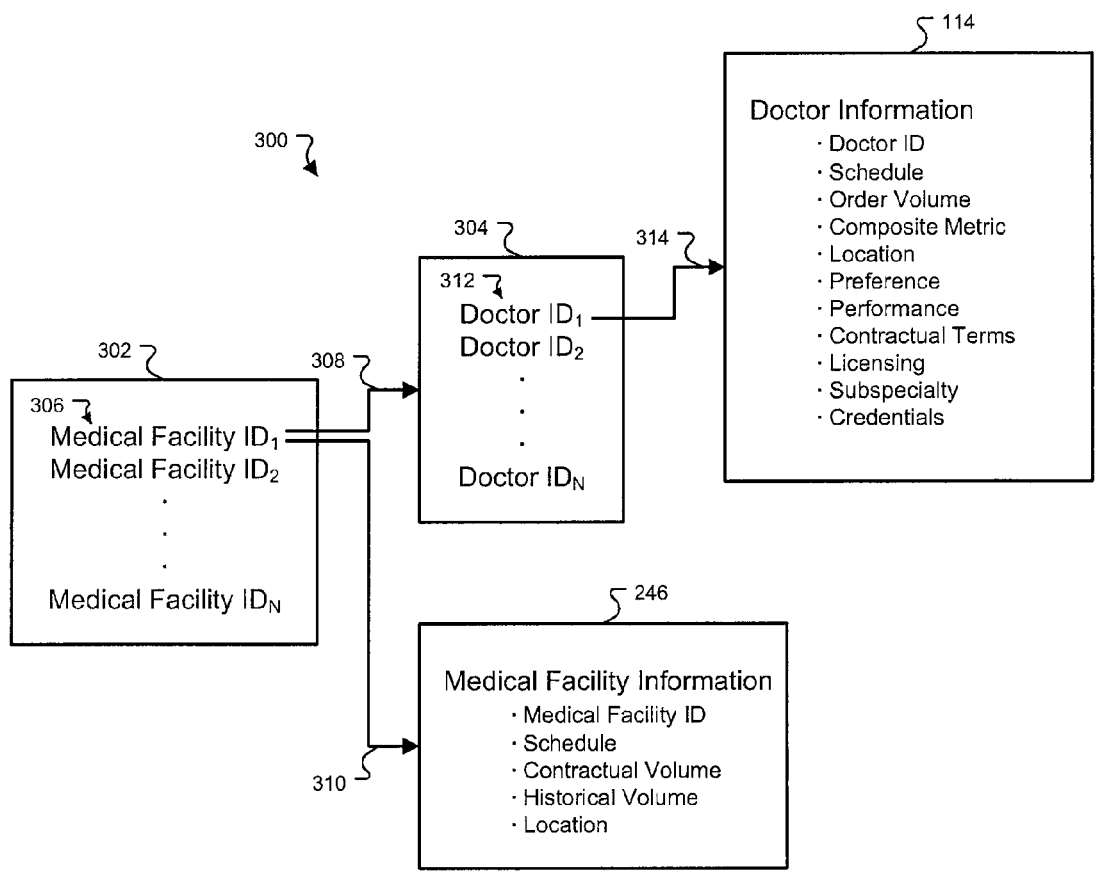
FIG. 3 is a schematic diagram of tables used by a workflow module to assign medical requests.

A data module 112 within the IO management system 102 stores doctor information 114 including a doctor identifier, doctor schedule information, an order volume, a doctor classification composite metric, doctor location information, preference information, performance information, and contract terms (shown in a FIG. 3). For example, a doctor may be identified within the data module 112 by a doctor ID. A doctor's schedule information may include times and dates that a doctor is scheduled to be available for reviewing medical requests. A doctor's order volume may indicate the number of medical requests that a doctor is capable of completing in a given period of time. A doctor's location may determine whether the doctor is allowed to review certain medical requests (e.g. doctors outside the United States may not be allowed to perform a final review of medical images). A medical facility's request for or refusal of a particular doctor may be indicated in the doctor preference information. A doctor's performance may be indicated by the accuracy of the doctor's reports or the satisfaction of medical facilities for which the doctor has reviewed medical requests. The contract terms of a doctor may specify a quota of medical requests the doctor is paid for regardless of the number of medical requests the doctor actually reviews. The contract terms may also specify a bonus rate for medical requests above the quota that are reviewed by the doctor.

A doctor's classification composite metric may be a combination of the doctor's compensation, either per medical request or a salary, and the contract terms of the doctor. In one implementation, a doctor compensated on a per medical request basis has a lower priority than a doctor that has a quota that has not yet been met. A doctor receiving higher bonus compensation than another doctor would have a lower priority than the other doctor when the two doctors have both reached their quotas. The classification composite metric reduces the overall cost of reviewing a set of medical requests while taking into consideration doctor compensation and doctor contractual terms.

A workflow module 116 receives the doctor information 114 and uses it along with the medical facility ID 110 to filter the medical request 108. In filtering the medical request 108, which is described in greater detail in association with FIGS. 2 and 3, the workflow module 116 identifies a doctor to receive the medical request 108. The IO management system 102 transmits the medical request 108 to the doctor system 106A, winch is accessible by the doctor identified during die filtering of the medical request.

To filter the medical request 108, the workflow module 116 transmits the medical facility ID 110 to the data module 112. The data module 112 uses the medical facility ID 110 to access and transmit the doctor information 114 associated with the medical facility ID. For example, the data module 112 may use the medical facility ID 110 as a key in a database table to locate all the doctors credentialed at a hospital specified by the medical facility ID 110. In this implementation, the data module 112 performs a first pass filter by providing to the workflow module 116 the doctor information 114, which contains a list of doctors credentialed at the medical facility 104. In another implementation, the returned list of doctors may be a subset of all the doctors credentialed at the medical facility 104. For example, the data module 112 may only return a list of credentialed doctors that are scheduled to work (as indicated by the doctor scheduling information stored in the data module 112) when the medical facility ID 110 is received by the data module 112.

Figure 2:
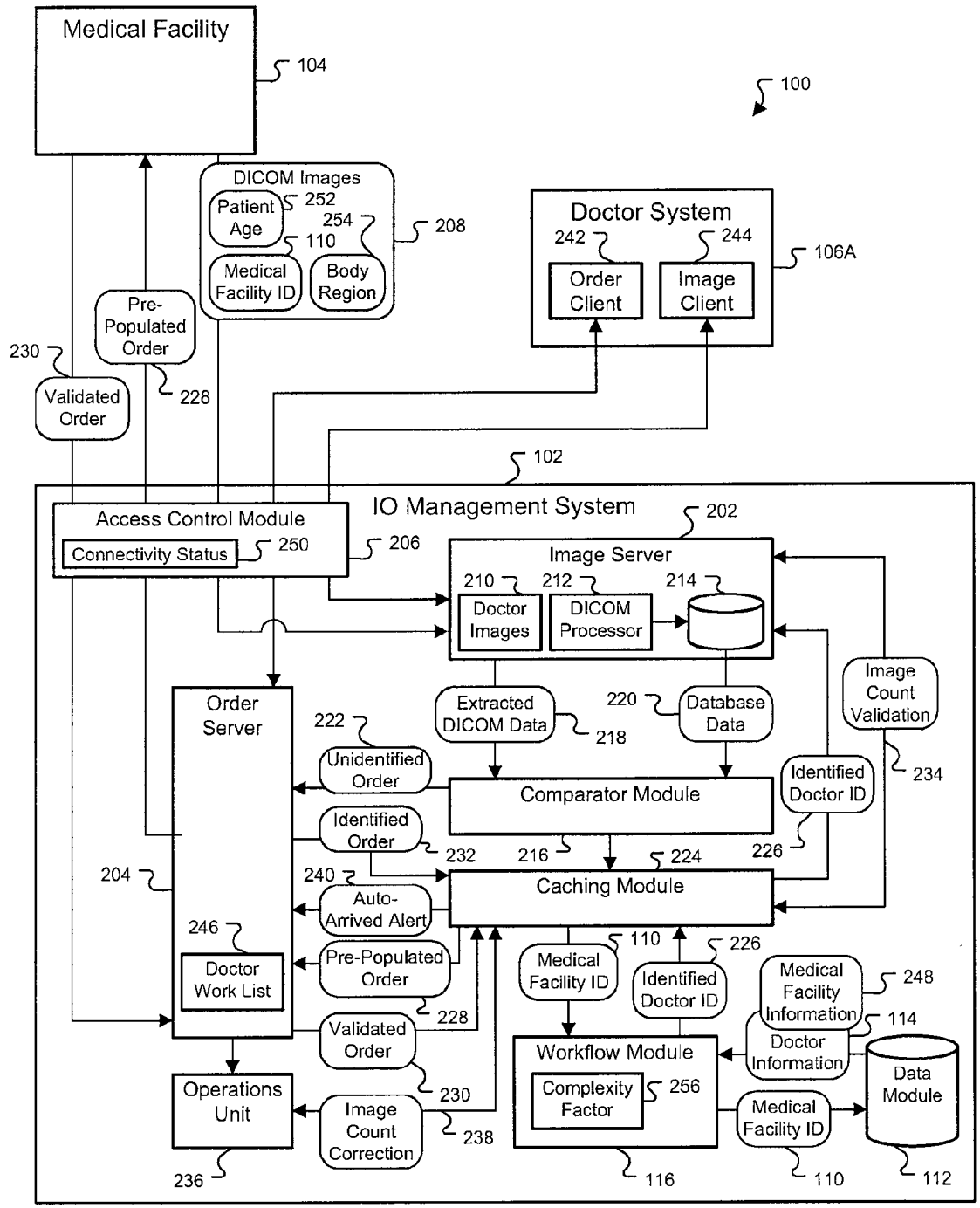
FIG. 2 is a block diagram of the system of FIG. 1 in more detail, according to one implementation.

FIG. 2 shows the system 100 of FIG. 1 in more detail according to one implementation. Within the IO management system 102, an image server 202 and an order server 204 receive images and orders, respectively, from the medical facility 104. The image server 202 and the order server 204 send the images and the orders to the doctor systems 106A-C for review by the doctors. An access control module 206 provides secure access to the IO management system 102 from the medical facility 104 and the doctor systems 106A-C.

As shown in FIG. 2, the medical facility 104 sends a medical request comprising DICOM images 208 to the IO management system 102. The image server 202 receives the DICOM images 208. The image server 202 may be part of a Picture Archive Communication System (PACS), which digitally stores, transmits, and displays medical images. The image server 202 may store the images as images 210. A DICOM processor 212 extracts DICOM data from the images and stores the DICOM data associated with the images in a database 214. The images are assigned an identifier that is stored in the database 214 and is used to access the images when needed for transmission or other purposes. When received, a compressor (not shown) may compress the images using a variety of compression algorithms to compress the images, such as JPEG, JPEGLS, JPEG2000, PNG, GIF, XBM, BMP, and TIFF.

The compressor may be implemented on the same computing device as the image server 202. In one implementation, the image compressor may be accessible by the software that executes the functions of the image server 202. For example, the image compressor may be a dynamic load library (dll) code segment stored on the same computing device and accessed by the image server 202. Alternatively, the compressor may be implemented on a separate computing device from the image server 202. For example, the compressor may be accessible to software that executes the functionality of an Internet server, which is resident on a separate machine from the image server 202. The Internet server may access the compressor whenever it receives images from the image server 202 for transmission to the network.

Additionally, the database 214 and the images 210 may be stored at the image server 202. For example, the images and database may be stored on same machine that executes the image server software. This may simplify the operation and maintenance of the software. Alternatively, the images and database may be stored on a different machine from the image server. For example, the database may be installed on its own machine that has increased security protections and is isolated from the network in order to protect the medical data stored in the database. Similarly, the images may be installed on a separate machine that provides more storage capacity and specialized hardware that facilitates quick and efficient retrieval and storage of the images, After the workflow module assigns the orders and corresponding images to the selected doctors, the image server 202 may transmit the compressed images over the network to the doctor systems 106A-C.

A comparator module 216 receives extracted DICOM data 218 and database data 220 from the image server 202. The image server extracts the original DICOM data from the images 210 again and transmits it to the comparator module 216 for comparison with the database data 220. The comparison is used to determine if the DICOM processor 212 stored the extracted data correctly and under the correct patient name. For example, if the medical facility ID 110 provided by the medical facility 104 is not unique within the database 214 the workflow module 116 may be unable to provide the correct ID to the data module 112 to filter the medical request. In addition, if a patient name included in the database data 220 and associated with the medical request does not match a patient name specified in the DICOM data 218, then the medical request may be incorrectly associated with the patient. If the medical request is incorrectly associated, then the comparator module 216 sends an unidentified order 222 to the order server 204 for correction. Otherwise, the comparator module 216 provides the medical facility ID 110 derived from the DICOM data included in the medical request to a caching module 224.

The caching module 224 caches information related to the medical request. The caching module 224 transmits the medical facility ID 110 to the workflow module 116. The workflow module transmits the medical facility ID 110 to the data module, which uses the facility ID 110 to access doctor information for doctors credentialed at a medical facility specified by the facility ID. The data module 112 then returns the doctor information to the workflow module 116. Additionally, the data module may return medical facility information 248, such as how many medical requests per day the facility is contracted to request. The workflow module then performs filtering algorithms to determine a doctor to receive the medical requests and returns an associated doctor ID 226 to the caching module. The specific filtering methods used by the workflow module 116 will be described in more detail below. The caching module 224 sends the identified doctor ID 226 to the image server 202. The image server 202 places the images included in the medical request in file folders, or directories, which are associated with the identified doctor ID 226. The caching module 224 generates a pre-populated order 228 using the extracted DICOM data 220 and sends the pre-populated order 228 to the order server 204. The pre-populated order may be an order for a medical service, such as a request to read radiology images that is pre-populated with patient and hospital information, such as the hospital and patient name.

The order server 204 sends the pre-populated order 228 to the medical facility 104. The medical facility 104 validates the information contained in the pre-populated order 228 and sends the validated order 230 to the order server 204. For example, staff at the medical facility 104 may check the pre-populated information for correctness and specify a number of images included in the medical request, a reason for the medical request, and a medical history of the patient. The order server 204 sends the validated order 230 to the caching module 224.

Unidentified orders 222 may also be corrected and then transmitted to the caching module 224. For example, personnel at the medical facility 104 may contact an operator with access to the order server. The medical facility personnel may provide the correct patient identification and other necessary information to correct the unidentified order 222. The operator may then correct the order 222, and the corrected order is transmitted to the caching module 224 as an identified order 232.

In another implementation, the unidentified orders 222 are corrected by transmitting a pre-populated order 228 to a "best guess" medical facility for confirmation. For example, the DICOM information associated with the unidentified order 222 may be used to generate a pre-populated order that includes the patient's name and other extracted information. If the originating facility is uncertain, the order server 204 may use fuzzy logic to determine the medical facility with the highest probability of being the originating facility. The order server may then transmit the pre-populated form with the patient information for confirmation. If the order server determines that more than one medical facility matches information from the DICOM header, the order server may send a pre-populated form to all the matching medical facilities. The confirmed order may then be transmitted to the caching module 224.

As images included in a medical request are received, the caching module 224 queries the image server 202 to determine if the correct number of images have been received, as indicated by arrow 234. If there are either too few or too many images received, then the caching module 224 refers the medical request to an operations unit 236 where the image count is corrected, as indicated by arrow 238. In one implementation, the image count is manually corrected by an operator that may contact personnel at the medical facility to inquire about the image count. When the image count is correct, the caching module 224 sends to the order server 204 an auto-arrived alert 240, and the order associated with the received medical images is placed in the doctor work list 246 associated with the doctor assigned to review the medical request.

The order server 204 sends the validated order 230, which is in the doctor's work list 246, to the order client 242 at the doctor system 106A. The image server 202 transmits the images to an image client 244 at the doctor system 106A. The doctor system 106A is associated with the identified doctor ID 226 and it is accessible by the identified doctor. The doctor may then review the images 208 and the order 230 associated with the medical request. The doctor generates a report based on the review and the report is sent to the medical facility 104, either directly or through the IO management system (not shown).

In filtering the medical requests, die workflow module 116 may use the doctor information 114 and the medical facility information received from the data module 112.

FIG. 3 shows data tables 300 contained in the data module 112. The data tables 300 include a list of medical facility IDs 302, a list of doctor IDs 304, the doctor information 114, and the medical facility information 248. Each medical facility ID is associated with a list of doctor IDs corresponding to doctors credentialed at that medical facility. Here, a first medical facility ID 306 is associated with the list of doctor IDs 304, as indicated by arrow 308. Each medical facility ID is associated with medical facility information. Here, the first medical facility ID 306 is associated with the medical facility information 248, as indicated by arrow 310. Each doctor ID is associated with doctor information. Here, the first doctor ID 312 is associated with the doctor information 114, as indicated by arrow 314.

The doctor information 114 may include data as described in association with FIG. 1. The doctor information 114 may also include credentialing and subspecialty information. In one implementation, the workflow module 116 may use the credentialing, the subspecialty information, or both to filter the medical requests. For example, a doctor that is not credentialed at the medical facility 104 will not be allowed to review medical requests from the medical facility 104. A doctor having a subspecialty in a particular type of medical request, such as a review of a magnetic resonance imaging (MRI), will be selected over another doctor having similar information, but no subspecialty in MRI reviews. In another implementation, the data module returns the entire doctor list 304. The entire list of doctors may be eligible to review the images because all doctors in the list 304 are credentialed at the medical facility associated with the facility ID 306.

The medical facility information 248 includes schedule information, location information, or both. The workflow module 116 may use the medical facility schedule information, the medical facility location information, or both to filter the medical requests. For example, a medical request received from the medical facility 104 outside of its scheduled service time may be categorized as an unidentified order 222, which prompts staff at the IO management system 102 to investigate the medical request. In another example, if the medical facility 104 is located within the United States and the medical request is a final reading of medical images, then a doctor located within the United States must be assigned to the medical request.

Referring again to FIG. 2, the access control module may monitor a connectivity status 250 of the medical facility 104 or the doctor systems 106A-C. The connectivity status 250 may indicate whether an encrypted network connection used by the medical facility 104 or the doctor systems 106A-C is operational. The workflow module 116 may use the connectivity status 250 of the medical facility 104 or the doctor systems 106A-C when filtering the medical requests. For example, the workflow module 116 may determine from the connectivity status 250 that the network connection to the doctor system 106A is not operational. The workflow module 116 may prevent medical requests from being assigned to the doctor associated with the doctor system 106A and assign the medical requests to the next doctor available based on the filtering rules.

The workflow module 116 may monitor the doctor work list 246 to determine the number of medical requests assigned to and not yet completed by the doctor. The workflow module 116 may use the number of incomplete medical requests to filter the next medical request. For example, a doctor with a high number of incomplete medical requests may have a lower chance of being assigned another medical request than a doctor with a low number of incomplete medical requests.

The DICOM images 208 may include information in DICOM headers, such as a patient age 252 and a body region 254. The workflow module 116 may determine a complexity factor 256 of the medical request based on the patient age 252, the body region 254, and the medical facility ID 110. For example, an image depicting a head or a chest may be more difficult for a doctor to review than an image depicting a forearm or leg. In addition, a medical request for a patient less than two years of age or over 75 years of age may be more difficult to review than a medical request for a patient that is 25 years old. Also, some medical facilities associate with a medical facility ID 110 may consistently transmit complex or difficult medical requests. Some or all of these factors may be combined to generate the complexity factor 256.

In one implementation, the workflow module 116 assigns weights to each of the components used to calculate the complexity factor 256. The weights may range from −1 to 1, with −1 being associated with less complexity and 1 with more complexity. For example, a patient that is 72 years old may have a weighting of 0.9, which indicates the case is more complex. In contrast, a 30 year old patient may have a weighting of −0.9, which indicates the case is less complex. The complexity factor may be the sum of the weightings for each component.

The workflow module 116 may use the complexity factor 256 to prevent a doctor from accepting only those medical requests that are easy. If the average complexity of the medical requests in the doctor work list 246 is low, then the workflow module 116 may assign only complex medical requests to the doctor until the average complexity of the doctor work list 246 meets a threshold. Similarly, if a doctor has accepted several complex medical requests, the workflow module may assign requests with a lower complexity factor to that doctor.

In one implementation, the threshold may be a single number that is compared with the sum of all the complexity factors. For example, a doctor may accept three difficult cases, each with a complexity factor of 2.9, and live simple cases, each with a complexity factor of −0.7. This means that the doctor has a complexity total of 5.2. If the threshold is 10, the workflow module may assign the doctor difficult cases until the threshold is met. If the threshold is exceeded, the workflow module may assign the doctor simple cases until the complexity total reaches or comes within a predefined range of the threshold. In another implementation, the threshold may be a number of studies that exceed a defined complexity factor. For example, if the doctor accepts four cases per hour with complexity factors over 2.5, the workflow module will assign simpler cases with complexity factors under −1.2 to the doctor until the hour is over.

In one implementation illustrating how the workflow module 116 obtains and uses the doctor information and the medical facility information to filter requests, the medical facility 104 sends images to the image server 202. The images include DICOM header information recording the patient's age, the body region with which the images are associated, and the medical facility ID.

The image server 202 extracts the DICOM information listed above and transmits it to the workflow module 116. The workflow module transmits the medical facility ID to the data module 112, where it is used to locate an entry that matches the facility ID. The matching entry may have a list of doctor identifiers that are credentialed at the medical facility specified by the medical facility ID. The doctor identifiers, in turn, may have doctor information, such as schedule information, volume information, performance information, and a complexity total, associated with each doctor identifier's entry. The data module 112 may then return to the workflow module the doctor identifiers of the doctor's credentialed at the identified hospital and the associated doctor information.

The workflow module may then begin the filtering process with a first of several rules that are applied to determine which doctor to assign the medical requests to for review. For example, the first filter rule may determine which of the credentialed doctors is available to accept medical requests using the doctors schedule information, which indicates the doctors that are currently on-call to accept requests.

Then the workflow module may apply a second rule that determines which of the on-call doctors have a functioning network connection to the IO management system 102. The on-call doctors that are currently connected (as monitored by the workflow module) will remain in a pool of doctors eligible to receive the medical request, while the doctors that are not actively connected are eliminated from the pool.

The next rule may consider the volume of medical request the doctors have currently accepted, but not completed (as indicated by the volume information received from the data module). In one implementation, the doctors with the least volume will be favored with a weighting factor over doctors with higher volume. For example, the workflow module may assign a weighting factor that favors doctor A over doctor B if doctor A has four accepted but incomplete medical requests, and doctor B has five accepted but incomplete medical requests.

The next filter rule may consider performance of the doctors, such as the average time it takes from acceptance to completion of a request (as indicated by the performance information received from the data module). In one implementation, the doctors with the shortest performance times are favored over doctors with longer performance times. In another implementation, the filter rule may be used in cooperation with the volume filter rule to determine a weighting for each doctor. If doctor A has a volume of four, and doctor B has a volume of five, the workflow module may still assign a weighting that favors doctor B over doctor A because doctor B has performance information that indicates doctor B will complete the medical requests in less time than doctor A. For example, if doctor A can complete four medical requests in an hour, but doctor B completes five medical requests in 50 minutes, doctor B is assigned a favored weighting because doctor B will be ready to review another medical request before doctor A, despite the fact that doctor B as more medical requests.

Additionally, the workflow module may implement a complexity filter that calculates a complexity factor for the medical request and assigns a weighting that favors or disfavors a doctor depending on the doctor's complexity total, which reflects the complexity of the cases that the doctor has accepted in the past, The workflow module may calculate the complexity factor for the medical request in a manner similar to the manner described above. The workflow module compares the doctor's complexity total to a threshold value, which is also described above. The workflow module then assigns a weight favoring or disfavoring each doctor depending on whether the doctor's complexity total reaches a threshold value and whether the medical request to be assigned is complex or simple as determined by the workflow module.

For example, the workflow module determines that the medical request is complex based on the age of the patient, the body region scanned, and the originating medical facility, The workflow module then determines that doctor A has not met the threshold, which indicates the doctor has not accepted did enough difficult cases. The workflow module will then assign a weight favoring the assignment of the medical requests to doctor A over other doctors that have exceeded the threshold, which indicates these doctors have accepted more difficult cases than doctor A.

After the workflow module applies the filter rules, the module sums the weighting factors for each of the doctors remaining in the assignment pool. The workflow module then selects the doctor with the highest weighting to receive the medical request.

Figure 4:
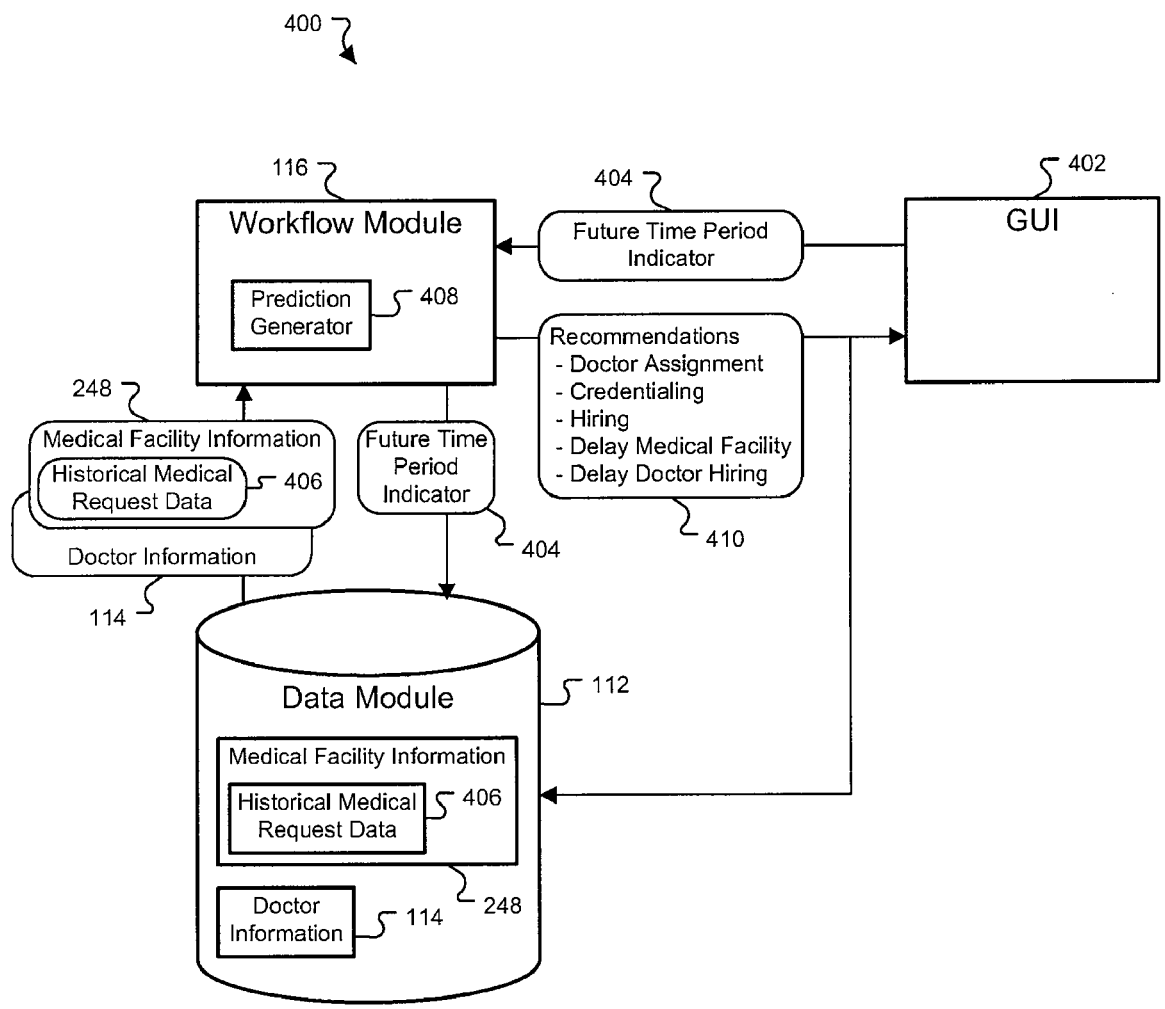
FIG. 4 is an exemplary block diagram of a portion of an image order management system that predicts an amount and origin of future medical requests.

FIG. 4 shows a system 400 that may be included in the IO management system 100. The system 400 is capable of predicting an amount and origin of future medical requests. This information, in turn, may be used to ensure enough doctors are available to handle the predicted number and type of medical requests. Additionally, the information may be used to identify if more medical requests are needed to fully utilize the predicted amount of doctors available to review the requests. The system 400 includes a graphical user interface (GUI) 402, the workflow module 116, and the data module 112.

More specifically, a user uses the GUI 402 to enter an input that indicates a future time period 404 for the prediction. The indicator 404 may describe a particular date in the future. The workflow module 116 receives the future time period indicator 404. The workflow module 116 queries the data module 112 using the indicator 404. The data module returns medical facility information 248 and doctor information 114 associated with the future time period indicator 404. The medical facility information 248 may include data describing all of the medical facilities that are scheduled to submit medical requests on the date and time in the future. The doctor information 114 may include data describing all of the doctors that will be online and scheduled to work on the date in the future. Here, the medical facility information 248 also includes historical medical request data 406.

For example, the future time period indicator 404 may indicate a particular day of the week within the following week, such as next Wednesday. The data module 112 may return historical medical request data 406 information regarding medical requests received from each medical facility for the two previous Wednesdays. The data module 112 also returns the doctor information 114 and the other medical facility information 248 previously described for filtering medical requests.

A prediction generator 408 in the workflow module 116 may use the historical medical request data 406 to generate a prediction for the amount and origin of medical requests occurring during the future time period. The prediction may indicate the average number of medical requests received per hour from a particular medical facility on a particular day of the week.

In another implementation, the prediction generator 408 uses contractual information associated with each of the medical facilities to generate the prediction. For example, the prediction generator may use an indicator specifying a future timer period to determine what facilities are contractually obligated to submit requests during the period. The generator may transmit the indicator to the data module 112, which returns the medical facility ID's of facilities scheduled to submit request and the information associated with the medical facilities including contract terms. The generator may create a prediction based on how many requests each medical facility has contracted to submit.

The allocation may be an approximately equal division of requests per hour. For example, if a medical facility is contracted to submit 40 medical request on a day specified by the indicator, the generator may allot a portion of the requests to each hour that the medical facility is contracted to submit requests (e.g., 5 requests allocated to 7 PM, 5 requests to 8 PM, etc.). Alternatively, the generator may allocate the requests on a bell curve model so that fewer of the requests are allocated near the beginning and the end of the scheduled submission hours, and more requests are allocated during the intermediate hours.

Figure 5:
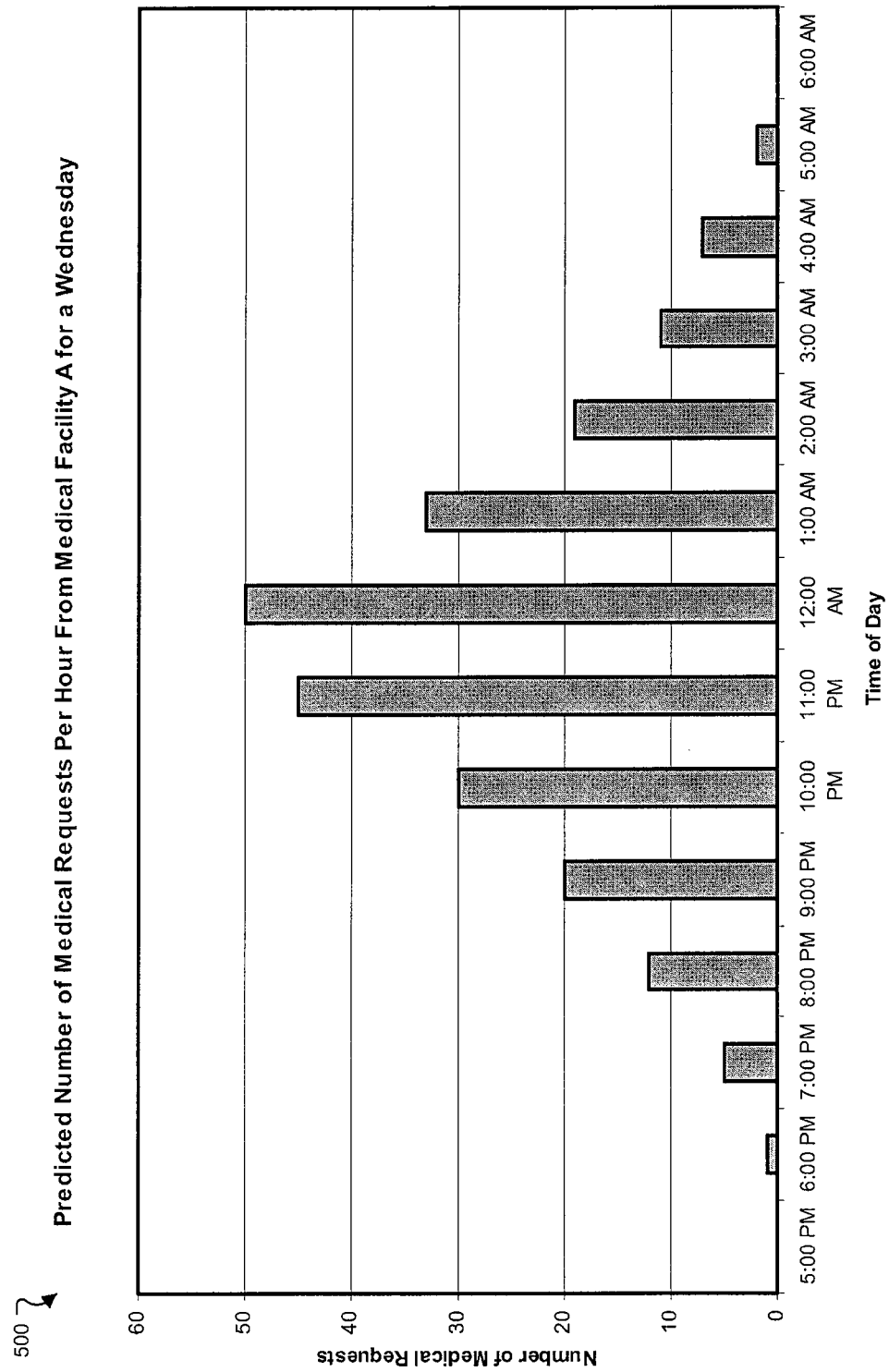
FIG. 5 is a graph showing an exemplary prediction from a prediction generator implemented at the image order management system.

As shown in FIG. 5, the prediction generated by the prediction generator 408 may be illustrated using a graph 500 including the number of medical requests per hour from a particular medical facility for a particular day of the week. Here, the graph 500 shows the number of medical requests per hour from Medical Facility A for the two previous Wednesdays. Based on the historical medical request data 406 for Medical Facility A, one can see that on average Medical Facility A begins to send medical requests at 6:00 PM. The number of medical requests from Medical Facility A peaks at 12:00 AM and Medical Facility A no longer sends medical requests after 5:00 AM on the morning after a Wednesday.

Referring again to FIG. 4, the workflow module 116 assigns the future medical requests to doctors in a similar manner as described in FIGS. 1 and 2. Each predicted medical request is processed as if it had been received by the IO management system 102. The workflow module 116 may use the doctor information 114, including doctor performance information, such as turnaround time for reviewing medical requests, to determine how long a medical request should remain in a doctor's work list. New medical requests may be added to the doctor's work list based on the doctor's historical rate of the fulfilling medical requests.

In some implementations, the medical facility information 248 is associated with medical facilities that are not yet active within the system 100. The prediction generator 408 may use information within the medical facility information 248, such as the date that a medical facility will become operational within the system 100, to make its prediction. If the future time period occurs after a new medical facility will become active, then the prediction generator 408 may use an average of the other medical facilities to determine the number of medical requests the medical facility is likely to transmit. The prediction may indicate an average number of requests generated in the past by a typical medical facility during the indicated time period. For example, a medial facility may be scheduled to send medical requests for the first time during the indicated time period. In this situation, the medical facility will not have a set of past medical requests which the prediction generator 408 may use to generate a prediction, To mitigate this problem, the prediction may be based on an average of the number of combined medical requests submitted by other medical facilities during the indicated time period. For instance, if 5 hospitals send 40 requests at 7 PM last Wednesday, then the average for last Wednesday would be 8 requests at 7 PM. The prediction based on the average requests submitted by the other facilities serves as a substitute when historical information for requests is not available for a particular medical facility.

In some implementations, the workflow module 116 recursively reassigns the future medical requests to the doctors until the assignments produce an optimal assignment. The workflow module 116 may determine the optimal assignment based on whether a value associated with assignment is below a threshold or within a defined tolerance range. A particular set of choices for doctor assignments may result in one or more medical requests that cannot be assigned to a doctor. For example, a medical request from Medical Facility A may remain unassigned if the only doctor scheduled to work during that time who is credentialed at Medical Facility A already has a full work list. The workflow module 116 may go back and reassign the medical requests. During the reassignment, the workflow module 116 may make a different choice regarding medical requests assigned to the doctor credentialed at Medical Facility A.

A reiterative assignment process may continue until a threshold is met. For example, the threshold may be that zero medical requests are left unassigned. The assignment process will go through multiple iterations until a state is reached where all the medical requests are assigned. Alternatively, the reiterative assignment process may continue until a certain number of iterations have been performed. After this number is reached, the state with the lowest number of unassigned medical requests may be selected, and a recommendation (discussed in greater detail below) may be generated that informs a user what actions the user needs to take to avoid unassigned medical requests, such as hire a doctor credentialed at the hospital or hospitals with the unassigned request or requests.

In some implementations, the workflow module 116 generates recommendations 410 that may be based on the predictions. For example, if attempts at reassignment identify predicted medical requests that can not be assigned because doctors are not available to review the requests from a particular medical facility, then the workflow module 116 may recommend that more doctors be credentialed at the medical facility. If there are not enough doctors to review all of the medical requests even if the active doctors are credentialed at facilities with unassigned medical requests, then the workflow module 116 may recommend that more doctors be hired. If the work lists of doctors are consistently low, then the workflow module 116 may recommend that more medical facilities be recruited for the system 100.

In addition, the workflow module 116 may recommend that the integration of new doctors be delayed if the workflow module makes predictive assignments that indicate active doctors do not have enough medical requests to review. For example, if the predicted assignments indicate that each of the existing doctors is only assigned 45 medical requests in a shift, the workflow module may recommend that new doctors should not be allowed to enter the system until the existing doctors are each assigned 55 medical requests in a shift. Similarly, the workflow module 116 may recommend that new medical facilities be delayed if the workflow module generates predictive assignments that indicate active doctors have too many medical requests to review. For example, if the predicted assignments indicated that each of the doctors is assigned 100 medical requests in a shift, the workflow module may recommend that new medical facilities should not be allowed to enter the system until more doctors are hired.

In some implementations, the workflow module 116 stores and uses the previously predicted assignments when the future time period occurs. The workflow module 116 may use the predicted sequence of medical request assignments as a starting point when assigning medical requests in real-time. If the predicted assignment does not apply or is invalid based on the current state of the system 100, the workflow module 116 may revert to the filtering rules as described in FIGS. 1 and 2. For example, when a medical request is received by the IO management system, the workflow module may make an assignment based on the stored predicted assignment without reapplying any of the filtering rules. If the current state of the system 100 is different from the predicted state of the system (e.g., one of the on-call doctors is not currently connected, an additional hospital is submitting medical requests, etc.), then the workflow module 116 uses the filter rules to make new assignments instead of using the predicted assignments.

Figure 6:
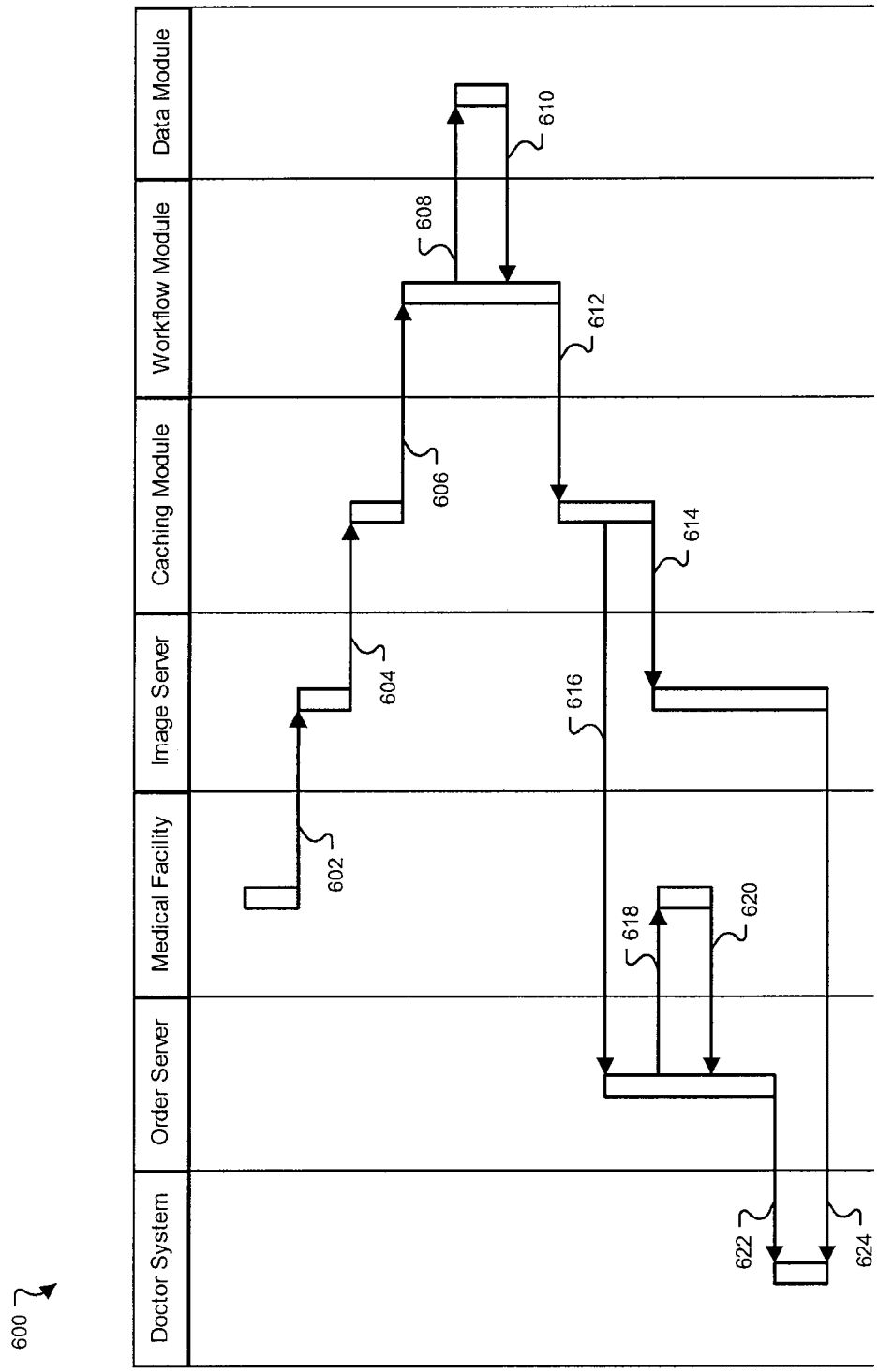
FIG. 6 is a sequence diagram of exemplary operations that can be performed to assign medical requests to doctor systems.
Figure 7:
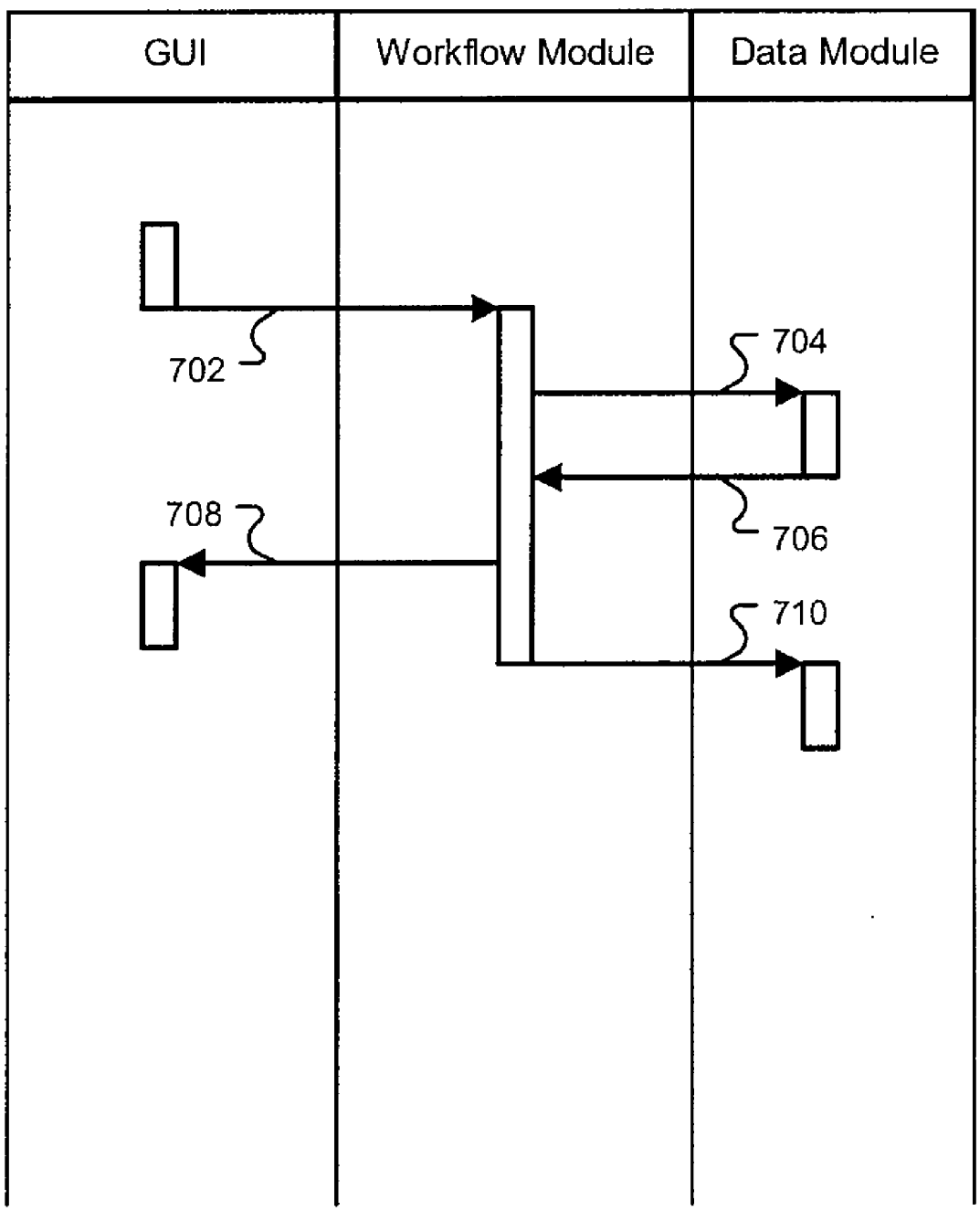
FIG. 7 is a sequence diagram of exemplary operations that can be performed to predict an amount and origin of future medical requests.

FIGS. 6 and 7 are sequence diagrams illustrating exemplary methods 600 and 700, respectively, for assigning medical requests to doctor systems and predicting future medical requests, respectively. Generally, the following description focuses on the operation of the IO management system 102 within the system 100. However, the operations contemplate using any appropriate combination and arrangement of logical elements implementing some or all of the described functionality.

FIG. 6 shows an exemplary sequence of operations 600 that the system 100 can perform to assign medical requests to doctor systems. The operations 600 begin with the medical facility 104 sending a medical request, such as the DICOM images 208, as indicated by arrow 602. The image server 202 within the IO management system 102 receives the DICOM images 208.

The image server 202 stores the DICOM images 208 and extracts DICOM data 218 from the DICOM images 208. The extracted DICOM data 218 is stored in a database 214. As more images in the medical request are received, the database data 220 is compared to the raw (not yet stored in database 220) extracted DICOM data 218. If they do not match, then the medical request is invalid and the image server 202 sends the unidentified order 222 to the order server 204, Otherwise, the DICOM images 208 are sent to the caching module 224, as indicated by arrow 604.

The caching module 224 sends the medical facility ID 110 contained in the DICOM images 208 to the workflow module 116, as indicated by arrow 606. The workflow module 116 uses the medical facility ID 110 to query the data module 112, as indicated by arrow 608.

The data module 112 returns the doctor information 114 to the workflow module 116, as indicated by arrow 610. The doctor information 114 may include a list of doctors and information associated with the doctors, such as the doctor's schedule, order volume, and contractual terms. The data module 112 may also return medical facility information 248, such as a medical facility location and a medical facility schedule.

The workflow module 116 filters the medical request to assign a doctor to the medical request. The filtering may be based on doctor information 114 and medical facility information 248 as described in association with FIGS. 1 and 2. In some implementations, the workflow module 116 may assign more than one doctor to a medical request or the workflow module 116 may later reassign the medical request. This double and reassignment of medical requests decreases the probability that a request will remain incomplete for an unacceptable period of time.

For example, a backup doctor may always be assigned in addition to the normally assigned doctor or if a medical request is not completed in a certain amount of time, the workflow module 116 may reassign the medical request to another or an additional doctor. For example, the workflow module may assign the medical request to doctor #1 and not to doctor #2. However, reassignment may include revoking the assignment of the medical request to doctor #1 and assigning the medical request to doctor #2.

Alternatively, the reassignment may include assigning the medical request to doctor #2 as well as to doctor #1. The workflow module 116 sends the identified doctor ID 226 to the caching module 224, as indicated by arrow 612.

The caching module 224 creates a pre-populated order 228 using the extracted DICOM data 218. The caching module 224 sends the identified doctor ID 226 to the image server 202 and the caching module 224 sends the pre-populated order 228 to the order server 204, as indicated by arrows 614 and 616, respectively.

The order server 204 sends the pre-populated order 228 to the medical facility 104, as indicated by arrow 618. The medical facility 104 validates the pre-populated order 228 and sends the validated order 230 to the order server 204, as indicated by arrow 620. The validation may include specifying a total number of images in the medical request, the reason for the medical request, and a medical history of the patient.

The order server 204 sends the validated order 230 to the caching module 224 where the expected number of images in the medical request is compared to the number of images received. If all of the images are received, the order server 204 places the validated order 230 in the work list 246 of the identified doctor and transmits the validated order 230 to the doctor system 106A, as indicated by arrow 622. The image server 202 places the DICOM images 208 in the doctor's directory associated with the identified doctor ID 226. The image server 202 sends the DICOM images 208 to the doctor system 106A, as indicated by arrow 624.

Again, FIG. 7 is a sequence diagram that illustrates an exemplary method 700 for predicting future medical requests. The operations 700 begin with the user input of a future time period indicator, such as a day or week in the future, A user may make the input through the GUI 402. The workflow module 116 receives the future time period indicator 404, as shown by arrow 702.

The workflow module 116 queries the data module 112 using the future time period indicator 404, as indicated by arrow 704. For example, the workflow module 116 may request, using the future time period indicator 404, all of the historical medical request data 406 for a particular day. The historical medical request data 406 may include an indicator of all the medical requests sent by the selected medical facilities on the particular day in prior weeks, months, or years. The medical facilities are selected based on their schedules and their online status. A medical facility is selected if it is scheduled to submit medical requests and it is online during the future time period.

The data module 112 returns the historical medical request data 406 associated with the future time period indicator 404, as indicated by arrow 706. The data module 112 also returns the doctor information 114 and the medical facility information 248, which is used by the workflow module 116 to assign the medical requests to a selected doctor.

The workflow module 116 uses the historical medical request data 406 to generate a prediction of an amount and origin of medical requests that will occur during the future time period. The workflow module 116 uses the assignment rules described in FIGS. 1 and 2 to assign all of the predicted medical requests for the future time period. The workflow module 116 may output recommendations 410 based on the assignments to a user of the GUI 402, as indicated by arrow 708.

The workflow module 116 may store the assignment information or the recommendations 410 in the data module 112. The workflow module 116 may use the assignments, the recommendations 410, or both when the future time period occurs.

A number of embodiments of the invention have been described. Nevertheless, it will be understood that various modifications may be made without departing from the spirit and scope of the invention. For example, in some implementations, the medical request 108 includes an image, an order, or both. The images may include representations of body parts, such as x-rays, computed tomography (CT) scans, and magnetic resonance imaging (MRI) scans. The images may also contain additional information, such as Digital Information in Communications and Medicine (DICOM) data. For example, the additional information may include the number of images in the transmission, the name of the patient, a name of the medical facility 104 and a name of a device within the medical facility 104 where the image was created. In some implementations, the medical facility ID 110 comprises the name of the medical facility and the name of the device that are contained in the information associated with the Image.

In other embodiments, the medical request may comprise information or images in a format other than DICOM format. For example, the medical request may comprise images in CTI ECAT 7 image format, which originated from CTI Molecular Imaging, Inc. of Knoxville, Tenn. A processor may extract the ECAT 7 data from image headers and store the information in the database 214. The processor may recognize the ECAT 7 file type by parsing the header and determining if a text string "MATRIX71" is at location 0 of the file. After the file is identified, information about the patient, such as name, age, and gender, may be extracted from the file along with additional information, such as the facility identifier.

The order may contain information about a patient, such as name, medical history, and the reason for creating the image.

The order may also include a description of an associated image, such as a pelvic abdominal scan, a number of images associated with the order, and an order type, such as preliminary or final read. The presence of the patient name and other patient information may enable a particular image to be linked with a particular order.

For example, a patient may come into the medical facility 104 with an injury or sickness and one or more images may be taken of the patient. This image may be obtained by an image data source in the medical facility 104 or it may be transferred to the image data source from another image capturing device. The image data source, in turn, may transmit the image to a computing device that sends it over a network to the IO management system 102. The image data source may also directly send an image to the IO management system 102 instead of first transmitting it to the computing device.

Medical facility personnel, such as a technician, may submit the order to a doctor or radiologist for reading the patient's images. The technician may enter the order into the computing device and send the order to the IO management system 102.

Medical facilities may send images and orders at the same time as one another or at different times. For example, in some implementations, the medical facility 104 sends the order before the images. In these implementations, the pre-populated order is not transmitted by the order server 204 to the medical facility 104, but the order is completed in full by personnel at the medical facility 104.

Images, orders, and reports may be sent over the same network or different networks, For example, the IO management system 102 may receive images and orders through a single T3 connection to the Internet, or the images may be received from the Internet through a T3 connection and the orders may be received through a modem connection. In another example, the IO management system 102 may receive an image and an order from a medical facility over the Internet and return a corresponding report to the medical facility over a fax connection.

Additionally, the images and orders may be sent separately or combined in one transmission. For instance, a computing device at a medical facility may use software that sends the orders and the images with a single application and single set of actions, or the medical facility may send the images using one application that sends one transmission and send the orders using a different application that sends a separate transmission.

The IO management system 102 may be implemented on a single computing device or on multiple computing devices, such as a server farm. In one implementation, the IO management system 102 may be disbursed over several servers that are connected through a network. This configuration may be advantageous by facilitating expansion of the system and flexibility in managing the flow of received and output images and orders.

Additionally, the doctor system may contain more than one computing device. For instance, there may be one computing device that accepts the images, decompresses them, and displays the images for the doctor. The other computing device may handle receiving the orders, displaying them to the doctor for acceptance, receiving the report from the doctor, and transmitting the report to the IO management system 102. The doctor may also not accept the order. For instance, if the doctor accessing the doctor system 106A is currently viewing an order previously received, the doctor may not be able to accept another order until the previous order is completed. In this situation, a different doctor may accept the order at another doctor system, such as the doctor system 106B. This is possible because the IO management system 102 may send the order to more than one doctor system. Once a doctor at one doctor system accepts an order, the IO management system 102 may remove the order from the other doctor systems.

In another embodiment, the prediction generated by the prediction generator 408 is based on long-term patterns, such as seasonality. The prediction may incorporate the average number of medical requests submitted by medical facilities during the month or week of the preceding years relative to the time period indicator. For example, if the indicator is for a day in December 2005, the generator may generate a prediction for this day using the average number of requests submitted daily by medical facilities in December 2004. Additionally, the generator 408 may weight this prediction using a growth factor, which accounts for growth in submitted medical requests. For example, the generator may determine based on historical data associated with medical requests that the average number of submitted requests has grown on average 27 percent a year for the past year. Applied to the previous example, this growth factor may be used to increase the seasonal prediction for December 2005 so that it is 27 percent higher than it was in December 2004.

In yet another embodiment, the prediction generator 408 may be used for scheduling. The generator may use the predicted medical requests to determine which doctors have the appropriate credentials to fulfill the predicted medical requests, and it may transmit a recommendation to a user that describes which doctors should be scheduled for which times, For example, if the prediction indicates that St. Mercy Hospital will submit 10 medical requests at 10 PM on Apr. 1, 2006, then the generator may recommend (or automatically schedule) that Doctor A, who is credentialed at St. Mercy, be scheduled to work at 10 PM on that day. Accordingly, other embodiments are within the scope of the following claims.

What is claimed is:

1. A method, comprising:
processing an electronic request for evaluation of a set of digital medical images produced from a medical imaging procedure at an originating medical imaging location; and
identifying, according to a workflow, a selected user from a plurality of users to conduct an evaluation of the set of digital medical images, the workflow comprising using a computer processor to perform the following acts:
obtaining one or more request attributes from data extracted from one or both of the electronic request and the set of digital medical images, the request attributes including an identifier of the originating medical imaging location;
obtaining parameterized information for the plurality of users, the parameterized information including user credentialing information and user licensing information for the originating medical imaging location obtained using the identifier of the originating medical imaging location;
filtering the plurality of users to one or more users available to conduct the evaluation of the set of digital medical images in connection with the electronic request, the filtering performed by comparing the request attributes to the parameterized information;
generating a ranking of users from one or more results of filtering the plurality of users, wherein one or more weighting factors used in the ranking of users include medical imaging location preferences obtained from the identifier of the originating medical imaging location; and identifying the selected user from the results of filtering the plurality of users using the ranking of users.

2. The method of claim 1, wherein the digital medical images are produced from one or more radiological imaging devices, wherein the electronic request for evaluation of the set of digital medical images includes a radiological read request, wherein the users available to conduct the evaluation of the set of digital medical images are radiologists, and wherein the workflow is conducted by a teleradiology provider.

3. The method of claim 1, further comprising:
routing information from the electronic request for evaluation of the set of digital medical images to the selected user according to results of the workflow; and
routing the set of digital medical images to the selected user according to results of the workflow.

4. The method of claim 1, wherein the parameterized information further includes one or more of: user schedule information, user classifications, user location information, user preference information, user performance information, user compensation metrics, user contract terms, user capacity, and user expertise; and wherein the weighting factors further include request timing, complexity of the electronic request for evaluation, and user request volume.

5. The method of claim 4, further comprising:
identifying the user performance information for users of the plurality of users, the user performance information comprising a completion time rating, a report accuracy rating, or a satisfaction rating; and
applying a performance ranking factor to the users using the user performance information.

6. The method of claim 1, wherein the electronic request for evaluation of the set of digital medical images includes a patient age, a body region, or both; and wherein generating a ranking of users comprises:
identifying a complexity total for users in the results of filtering the plurality of users and applying a complexity ranking factor to users using the complexity total, wherein applying the complexity ranking factor comprises:
comparing the complexity total to a complexity total threshold, calculating a complexity level for the evaluation of the set of digital medical images, using at least one of the patient age, the identifier of the originating medical imaging location, the body region, or combination thereof, and comparing the complexity level to a complexity level threshold, wherein:
when the complexity level is above the complexity level threshold, applying a preference for users having a complexity total below the complexity total threshold, and when the complexity level is below the complexity level threshold, applying a preference for users having a complexity total above the complexity total threshold.

7. The method of claim 6, wherein calculating the complexity level for the evaluation of the set of digital medical images comprises:
assigning an age complexity weight using the patient age;
assigning a body region complexity weight using the body region;
assigning a medical location complexity weight using the identifier of the originating medical imaging location; and
calculating a sum of the age complexity weight, the body region complexity weight, and the medical imaging location complexity weight.

8. The method of claim 6, wherein the complexity total is calculated by a sum of complexity level of all evaluations completed by users in the results of filtering the plurality of users during a set time period.

9. The method of claim 1, the workflow further comprising:
identifying the user credentialing information for users credentialed at the originating medical imaging location using the identifier of the originating medical imaging location;
identifying the user licensing information for users licensed for the originating medical imaging location using the identifier of the originating medical imaging location; and
wherein filtering the plurality of users to users available to conduct the evaluation includes filtering for identified users credentialed at and licensed for the originating medical imaging location.

10. The method of claim 1, further comprising:
identifying a backup user from the plurality of users to evaluate the set of digital medical images according to the workflow, the backup user having a second highest rank in the ranking of users; and
upon determination that the selected user failed to conduct the evaluation of the set of digital medical images within a specified timeframe:
routing the information from the electronic request for evaluation of the set of digital medical images to the backup user; and
routing the set of digital medical images to the backup user.

11. A non-transitory machine-readable storage medium including instructions, when performed by a machine, cause the machine to perform operations comprising:
processing an electronic request for evaluation of a set of digital medical images produced from a medical imaging procedure at an originating medical imaging location; and
identifying, according to a workflow, a selected user from a plurality of users to conduct an evaluation of the set of digital medical images, the workflow comprising:
obtaining one or more request attributes from data extracted from one or both of the electronic request and the set of digital medical images, the request attributes including an identifier of the originating medical imaging location;
obtaining parameterized information for the plurality of users, the parameterized information including user credentialing information and user licensing information for the originating medical imaging location obtained from the identifier of the originating medical imaging location;
filtering the plurality users to one or more users available to conduct the evaluation of the set of digital medical images in connection with the electronic request, the filtering performed by comparing the request attributes to the parameterized information;
generating a ranking of users from one or more results of filtering the plurality of users, wherein one or more weighting factors used in the ranking of users include medical imaging location preferences obtained from the identifier of the originating medical imaging location; and
identifying the selected user from the results of filtering the plurality of users using the ranking of users.

12. The non-transitory machine-readable storage medium of claim 11, wherein the digital medical images are produced from one or more radiological imaging devices, wherein the electronic request for evaluation of the set of digital medical images includes a radiological read request, wherein the users available to conduct the evaluation of the set of digital medical images are radiologists, and wherein the workflow is conducted by a teleradiology provider.

13. The non-transitory machine-readable storage medium of claim 11, the operations further comprising:
routing information from the electronic request for evaluation of the set of digital medical images to the selected user according to results of the workflow; and
routing the set of digital medical images to the selected user according to results of the workflow.

14. The non-transitory machine-readable storage medium of claim 11, wherein the parameterized information further includes one or more of: user schedule information, user classifications, user location information, user preference information, user performance information, user compensation metrics, user contract terms, user capacity, and user expertise; and wherein the weighting factors further include request timing, complexity of the electronic request for evaluation, and user request volume.

15. The non-transitory machine-readable storage medium of claim 14, further comprising:
identifying the user performance information for users of the plurality of users, the user performance information comprising a completion time ranking, a report accuracy rating, or a satisfaction rating; and
applying a performance ranking factor to the users using the user performance information.

16. The non-transitory machine-readable storage medium of claim 11, wherein the electronic request for evaluation of the set of digital medical images includes a patient age, a body region, or both; and wherein generating a ranking of users comprises:
identifying a complexity total for users in the results of filtering the plurality of users and applying a complexity ranking factor to users using the complexity total, wherein applying the complexity ranking factor comprises:
comparing the complexity total to a complexity total threshold, calculating a complexity level for the evaluation of the set of digital medical images, using at least one of the patient age, the identifier of the originating medical imaging location, the body region, or combination thereof, and comparing the complexity level to a complexity level threshold, wherein:
when the complexity level is above the complexity level threshold, applying a preference for users having a complexity total below the complexity total threshold, and when the complexity level is below the complexity level threshold, applying a preference for users having a complexity total above the complexity total threshold.

17. The non-transitory machine-readable storage medium of claim 16, wherein calculating the complexity level for the evaluation of the set of digital medical images comprises:
assigning an age complexity weight using the patient age;
assigning a body region complexity weight using the body region;
assigning a medical location complexity weight using the identifier of the originating medical imaging location; and
calculating a sum of the age complexity weight, the body region complexity weight, and the medical imaging location complexity weight.

18. The non-transitory machine-readable storage medium of claim 16, wherein the complexity total is calculated by a sum of complexity level of all evaluations completed by users in the results of filtering the plurality of users during a set time period.

19. The non-transitory machine-readable storage medium of claim 11, the operations further comprising:
identifying the user credentialing information for users credentialed at the originating medical imaging location using the identifier of the originating medical imaging location;
identifying the user licensing information for users licensed for the originating medical imaging location using the identifier of the originating medical imaging location; and
wherein filtering the plurality of users to users available to conduct the evaluation includes filtering of identified users credentialed at and licensed for the originating medical imaging location.

20. The non-transitory machine-readable storage medium of claim 11, the operations further comprising:
identifying a backup user from the plurality of users to evaluate the set of digital medical images according to the workflow, the backup user having a second highest rank in the ranking of users; and
upon determination that the selected user failed to conduct the evaluation of the set of digital medical images within a specified timeframe:
routing the information from the electronic request for evaluation of the set of digital medical images to the backup user; and
routing the set of digital medical images to the backup user.

21. A method, comprising using a computer processor to perform the following acts:
accessing data related to medical imaging evaluation requests previously submitted by a plurality of medical imaging locations;
identifying, from the data, a historical volume of the medical imaging evaluation requests associated with one or more particular imaging locations of the plurality of medical imaging locations, the historical volume occurring during a prior time period;
generating a forecast volume of future medical imaging evaluation requests expected to be received from the one or more particular imaging locations during a future time period, the future time period correlating to the prior time period, and the forecast volume derived from the historical volume;
identifying one Or more assignment parameters for assignment of the future medical imaging evaluation requests to a plurality of available users during the future time period, the assignment parameters including one or more of:
user scheduling, expected user licensing approval, expected user credentialing approval, medical imaging location preference for certain users, user contract terms, one or more user compensation metric, one or more historical user performance metric, and additional medical imaging locations to be serviced, during the future time period; and
assigning, within a workflow, new medical imaging evaluation requests to the plurality of available users using a ranking of the plurality of available users derived from the assignment parameters.

22. The method of claim 21, wherein the medical imaging evaluation requests include radiological reading requests, wherein the plurality of available users are radiologists, and wherein the workflow is conducted by a teleradiology provider to assign the radiological reading requests to selected radiologists from the ranking of the plurality of available users.

23. The method of claim 21, further comprising:
identifying, within the user schedules, a list of scheduled users associated with the future time period;
identifying an assignment schedule including a lowest number of unassigned future medical imaging evaluation requests, wherein identifying the assignment schedule comprises:
(a) assigning requests of the forecast volume of future medical imaging evaluation requests to one or more of the scheduled users,
(b) creating a proposed assignment schedule using results of assigning the requests;
(c) determining a number of unassigned future medical imaging evaluation requests associated with the proposed assignment schedule, and
(d) storing the proposed assignment schedule,
wherein steps (a) through (d) are repeated for a plurality of iterations, each iteration including different assignments of users and future medical imaging evaluation requests;
storing the assignment schedule; and
determining, at the future time period, whether a list of available users corresponds to the scheduled users and a list of connected medical imaging locations corresponds to the plurality of medical imaging locations;
wherein assigning the new medical imaging evaluation requests to the plurality of available users within the workflow includes using the assignment schedule; and
wherein the future time period is of comparable length to the prior time period.

24. The method of claim 21, wherein the ranking of the plurality of available users includes:
determining a pending assignment volume for users of the plurality of available users and applying a volume weight for users having low pending order volumes;
determining an evaluation request quota for users of the plurality of available users and applying a quota weight for users currently below quota;
combining the volume weight and the quota weight for users of the plurality of available users into a total weight value; and
ranking the plurality of available users using the total weight value.

25. The method of claim 21, further comprising:
determining a number of licenses, credentials, or users needed to fulfill the forecast volume of the future medical imaging evaluation requests within the workflow.

26. The method of claim 21, wherein the forecast volume of the future medical imaging evaluation requests is generated in part using one or both of:
the historical volume of the medical imaging evaluation requests weighted by a calculated growth factor; and
a number of contractually obligated medical imaging evaluation requests per medical imaging location.

27. A non-transitory machine-readable storage medium including instructions, when performed by a machine, cause the machine to perform operations comprising:
accessing data related to medical imaging evaluation requests previously submitted by a plurality of medical imaging locations;
identifying, from the data, a historical volume of the medical imaging evaluation requests associated with one or more particular imaging locations of the plurality of medical imaging locations, the historical volume occurring during a prior time period;
generating a forecast volume of future medical imaging evaluation requests expected to be received from the one or more particular imaging locations of during a future time period, the future time period correlating to the prior time period, and the forecast volume derived from the historical volume;
identifying one or more assignment parameters for assignment of the future medical imaging evaluation requests to a plurality of available users during the future time period, the assignment parameters including one or more of:
user scheduling, expected user licensing approval, expected user credentialing approval, medical imaging location preference for certain users, user contract terms, one or more user compensation metrics, one or more historical user performance metrics, and one or more additional medical imaging locations to be serviced during the future time period; and
assigning, within a workflow, new medical imaging evaluation requests to the plurality of available users using a ranking of the plurality of available users derived from the assignment parameters.

28. The non-transitory machine-readable storage medium of claim 27, wherein the medical imaging evaluation requests include radiological reading requests, wherein the plurality of available users are radiologists, and wherein the workflow is conducted by a teleradiology provider to assign the radiological reading requests to selected radiologists from the ranking of the plurality of available users.

29. The non-transitory machine-readable storage medium of claim 27, the operations further comprising:
identifying, within the user schedules, a list of scheduled users associated with the future time period;
identifying an assignment schedule including a lowest number of unassigned future medical imaging evaluation requests, wherein identifying the assignment schedule comprises:
(a) assigning requests of the forecast volume of future medical imaging evaluation requests to one or more of the scheduled users,
(b) creating a proposed assignment schedule using results of assigning the requests;
(c) determining a number of unassigned future medical imaging evaluation requests associated with the proposed assignment schedule, and
(d) storing the proposed assignment schedule,
wherein steps (a) through (d) are repeated for a plurality of iterations, each iteration including different assignments of users and future medical imaging evaluation requests;
storing the assignment schedule; and
determining, at the future time period, whether a list of available users corresponds to the scheduled users and a list of connected medical imaging locations corresponds to the plurality of medical imaging locations;
wherein assigning the new medical imaging evaluation requests to the plurality of available users within the workflow includes using the assignment schedule; and
wherein the future time period is of comparable length to the prior time period.

30. The non-transitory machine-readable storage medium of claim 27, wherein the ranking of the plurality of available users includes:

determining a pending assignment volume for users of the plurality of available users and applying a volume weight for users having low pending order volumes;

determining an evaluation request quota for users of the plurality of available users and applying a quota weight for users currently below quota;

combining the volume weight and the quota weight for users of the plurality of available users into a total weight value; and ranking the plurality of available users using the total weight value.

31. The non-transitory machine-readable storage medium of claim 27, the operations further comprising:

determining a number of licenses, credentials, or users needed to fulfill the forecast volume of the future medical imaging evaluation requests within the workflow.

32. The non-transitory machine-readable storage medium of claim 27, wherein the forecast volume of the future medical imaging evaluation requests is generated in part using one or both of:

the historical volume of the medical imaging evaluation requests weighted by a calculated growth factor; and a number of contractually obligated medical imaging evaluation requests per medical facility.

* * * * *

UNITED STATES PATENT AND TRADEMARK OFFICE
CERTIFICATE OF CORRECTION

| | | |
|---|---|---|
| PATENT NO. | : 8,090,593 B2 | Page 1 of 1 |
| APPLICATION NO. | : 13/084379 | |
| DATED | : January 3, 2012 | |
| INVENTOR(S) | : Brent Backhaus et al. | |

It is certified that error appears in the above-identified patent and that said Letters Patent is hereby corrected as shown below:

In column 17, line 54, in Claim 6, delete "haying" and insert -- having --, therefor.

In column 18, line 52, in Claim 11, delete "plurality" and insert -- plurality of --, therefor.

In column 20, line 50, in Claim 21, delete "Or" and insert -- or --, therefor.

In column 20, line 60, in Claim 21, delete "serviced," and insert -- serviced --, therefor.

Signed and Sealed this
Thirteenth Day of March, 2012

David J. Kappos
*Director of the United States Patent and Trademark Office*